(12) United States Patent
Boussiengui-Boussiengui et al.

(10) Patent No.: US 8,729,338 B2
(45) Date of Patent: May 20, 2014

(54) METHOD OF MODIFYING THE CARBOHYDRATE CONTENT OF A PLANT

(75) Inventors: Gino Boussiengui-Boussiengui, Libreville (GA); Jens Kossmann, Somerset West (ZA)

(73) Assignees: Stellenbosch University, Stellenbosch (ZA); South African Sugarcane Research Institute, Mouth Edgecombe (ZA)

(*) Notice: Subject to any disclaimer, the term of this patent is extended or adjusted under 35 U.S.C. 154(b) by 0 days.

(21) Appl. No.: 13/496,468

(22) PCT Filed: Sep. 17, 2010

(86) PCT No.: PCT/IB2010/002331
§ 371 (c)(1),
(2), (4) Date: Mar. 15, 2012

(87) PCT Pub. No.: WO2011/033371
PCT Pub. Date: Mar. 24, 2011

(65) Prior Publication Data
US 2012/0180161 A1    Jul. 12, 2012

(30) Foreign Application Priority Data
Sep. 17, 2009    (ZA) .................. 2009/06506

(51) Int. Cl.
*A01H 5/00* (2006.01)
*C12N 15/113* (2010.01)

(52) U.S. Cl.
USPC .......................................... 800/285; 800/320

(58) Field of Classification Search
None
See application file for complete search history.

(56) References Cited

U.S. PATENT DOCUMENTS

| 6,573,426 B1 | 6/2003 | Falco et al. |
| 2009/0094717 A1 | 4/2009 | Troukhan et al. |

OTHER PUBLICATIONS

Wu et al, 2007, Plant Biotechnology Journal, 5:109-117.*
Waterhouse et al, 1998, PNAS, 95:13959-13964.*
Thomas et al, 2001, Plant J., 25:417-425.*
Geigenberger et al, 2005, The Plant Cell, 17:2077-2088.*
Extended European Search Report in corresponding European Application No. 10816769.3 mailed Feb. 7, 2013 (6 pages).
Notification Concerning Transmittal of International Preliminary Report on Patentability in corresponding PCT Application No. PCT/IB2010/002331 mailed Mar. 29, 2012 (6 pages).
Geigenberger et al., "Inhibition of de Novo Pyrimidine Synthesis in Growing Potato Tubers Leads to a Compensatory Stimulation of the Pyrimidine Biosynthetic Performance" *The Plant Cell*, vol. 17, 2077-2088, Jul. 2005.
Chuang et al., "Specific and heritable genetic interference by double-stranded RNA in *Arabidopsis thaliana*" PNAS, Apr. 25, 2000, vol. 97, No. 9, pp. 4985-4990.

* cited by examiner

*Primary Examiner* — Ashwin Mehta
*Assistant Examiner* — Jason Deveau Rosen
(74) *Attorney, Agent, or Firm* — Myers Bigel Sibley & Sajovec, PA

(57) ABSTRACT

A method of modifying at least one carbohydrate in a tissue of a plant is described. The method is typically applied to a sugarcane plant of the genus *Saccharum* method and includes the steps of inserting into a plant cell a gene silencing cassette which includes nucleic acid operably linked to transcription elements such as a monocotyledonous promoter for transcribing the nucleic acid in a plant cell, wherein transcription of the nucleic acid decreases activity of UMP synthase. The method further includes the steps of regenerating a transgenic plant from the plant cell and producing the tissue with increased carbohydrate content. Vectors for use therefor, as well as a transformed plant cell and a transgenic plant or plant part containing or derived from a transformed plant cell are also described.

27 Claims, 16 Drawing Sheets

Sequences producing significant alignments:

(Click headers to sort columns)

| Accession | Description | Max score | Total score | Query coverage | E value | Max ident | Links |
|---|---|---|---|---|---|---|---|
| XM 002456891.1 | Sorghum bicolor hypothetical protein (SORBIDRAFT_03g045930) mRNA, complete cds | 1286 | 1286 | 91% | 0.0 | 95% | G |
| NM 001148766.1 | Zea mays hypothetical protein LOC100274407 (LOC100274407), mRNA >gb\|BT042958.1\| Zea mays full-length cDNA clone ZM_BFc0070D11 mRNA, complete cds | 1085 | 1085 | 91% | 0.0 | 90% | G |
| BT009130.1 | Triticum aestivum clone wl1n.pk0029.c7:fis, full insert mRNA sequence | 1085 | 1085 | 91% | 0.0 | 90% | U |
| AY104150.1 | Zea mays PCO139907 mRNA sequence | 1085 | 1085 | 91% | 0.0 | 90% | U |
| NM 001112411.1 | Zea mays UMP synthase (UMPS), mRNA >gb\|AF277454.1\|AF277454 Zea mays UMP synthase (UMPS) mRNA, UMPS-1 allele, complete cds | 979 | 979 | 74% | 0.0 | 93% | UG |
| EU961333.1 | Zea mays clone 234591 uridine 5-monophosphate synthase mRNA, complete cds | 697 | 697 | 50% | 0.0 | 95% | U |
| AK331322.1 | Triticum aestivum cDNA, clone: WT007_D10, cultivar: Chinese Spring | 676 | 676 | 65% | 0.0 | 88% | |
| NM 001051947.1 | Oryza sativa (japonica cultivar-group) Os01g0951200 (Os01g0951200) mRNA, complete cds | 627 | 627 | 67% | 4e-176 | 85% | UG |
| AK069565.1 | Oryza sativa Japonica Group cDNA clone:J023023L08, full insert sequence | 627 | 627 | 67% | 4e-176 | 85% | UE |
| AF210324.1 | Oryza sativa clone C26554 UMP synthase (UMPS1) mRNA, complete cds | 627 | 627 | 67% | 4e-176 | 85% | UEG |
| AF210323.1 | Oryza sativa clone C26785 UMP synthase (UMPS1) mRNA, complete cds | 627 | 627 | 67% | 4e-176 | 85% | UG |

Figure 20A

| | | | | | |
|---|---|---|---|---|---|
| AF210322.1 | Oryza sativa clone C28243 UMP synthase (UMPS1) mRNA, partial cds | 627 627 67% | 4e-176 | 85% | U |
| AB031395.1 | Oryza sativa Japonica Group mRNA for UMP synthase 1, complete cds | 627 627 67% | 4e-176 | 85% | U G |
| NM_001051948.1 | Oryza sativa (japonica cultivar-group) Os01g0951400 (Os01g0951400) mRNA, complete cds | 625 625 65% | 1e-175 | 86% | U G |
| AK102468.1 | Oryza sativa Japonica Group cDNA clone:J033094F19, full insert sequence | 625 625 65% | 1e-175 | 86% | U G |
| AF210325.1 | Oryza sativa clone C23033 truncated UMP synthase (UMPS2) mRNA, partial cds | 625 625 65% | 1e-175 | 86% | U |
| AB037418.1 | Oryza sativa Japonica Group UMPS2 mRNA for UMP synthase 2, complete cds | 625 625 65% | 1e-175 | 86% | U E |
| BT062894.1 | Zea mays full-length cDNA clone ZM_BFc0004N16 mRNA, complete cds | 568 568 65% | 2e-158 | 84% | |
| EU965215.1 | Zea mays clone 284568 mRNA sequence | 520 520 51% | 7e-144 | 87% | U |
| EU948257.1 | Zea mays clone 371964 mRNA sequence | 350 350 39% | 9e-93 | 85% | U |
| AP008207.1 | Oryza sativa (japonica cultivar-group) genomic DNA, chromosome 1 | 324 754 39% | 6e-85 | 94% | |
| AP003735.4 | Oryza sativa Japonica Group genomic DNA, chromosome 1, BAC clone:B1147A04 | 324 754 39% | 6e-85 | 94% | |
| U22260.1 | Nicotiana tabacum UMP synthase (pyr5-6) mRNA, partial cds | 285 285 59% | 3e-73 | 76% | U |
| EZ052207.1 | TSA: Zea mays contig53328, mRNA sequence | 222 222 22% | 2e-54 | 86% | |
| AF277455.1 | Nicotiana plumbaginifolia UMP synthase (UMPS) gene, UMPS-1 allele, complete cds | 100 100 9% | 1e-17 | 88% | |
| XM_001746767.1 | Monosiga brevicollis MX1 predicted protein MONBRDRAFT_32885 mRNA, complete cds | 71.3 71.3 7% | 8e-09 | 87% | G |

Figure 20B

```
#########################################
# Program: needle
# Rundate: Fri Jul 10 10:01:13 2009
# Align_format: srspair
# Report_file: /ebi/extserv/old-work/needle-20090710-1001128854.output
#########################################

#=======================================

# Aligned_sequences: 2
# 1: SWEETSORGHUM
# 2: SUGARCANE
# Matrix: EBLOSUM62
# Gap_penalty: 10.0
# Extend_penalty: 0.5

# Length: 976
# Identity:     834/976 (85.5%)
# Similarity:   834/976 (85.5%)
# Gaps:         103/976 (10.6%)
# Score: 4751.0

#=======================================

SWEETSORGHUM       1 CTGATTTTACACCAGATTTTGGCTCTGAGCTCCGCTCGATTGCTGAGAAG      50
                     |||||||||||||.|||||||||||||.||||||||||||||||||||||
SUGARCANE          1 CTGATTTTACACCTGATTTTGGCTCTAAGCTCCGCTCGATTGCTGAGAAG      50

SWEETSORGHUM      51 CACAACTTTCTGATCTTCGAAGACCGCAAGTTTGCTGACATTGGAAATAC     100
                     ||||||||..|||||||.||||||||||||||||||||||||||||||||
SUGARCANE         51 CACAACTTCTTGATCTTTGAAGACCGCAAGTTTGCTGACATTGGAAATAC     100

SWEETSORGHUM     101 AGTAACCATGCAATATGAAGGAGGAATATTCCGCATATTGGACTGGGCAG     150
                     |||.||||||||||||||||||||.|||||||||||||||||||||||.|
SUGARCANE        101 AGTGACCATGCAATATGAAGGAGGAGTATTCCGCATATTGGACTGGGCCG     150

SWEETSORGHUM     151 ATATTGTTAATGCGCATATAGTACCTGGACCTGGAATCGTAGATGGCTTG     200
                     |||||||||||||||||||||||||||||||||||||||.||||||||||
SUGARCANE        151 ATATTGTTAATGCGCATATAGTACCTGGACCTGGAATCATAGATGGCTTG     200

SWEETSORGHUM     201 AAGCTGAAGGGTTTGCCTAAAGGAAGAGGGCTACTTCTGCTCGCTGAGAT     250
                     ||||||||||||||||.|||||||||||||||||||||||||||||||||
SUGARCANE        201 AAGCTGAAGGGTTTGCCAAAAGGAAGAGGGCTACTTCTGCTCGCTGAGAT     250

SWEETSORGHUM     251 GAGCTCTGCTGGCAACCTTGCTCATGGAGATTACACTGCTGCTGCTGTAA     300
                     ||||||||||||||||||||||||||||||||||||||||||||||||||
SUGARCANE        251 GAGCTCTGCTGGCAACCTTGCTCATGGAGATTACACTGCTGCTGCTGTAA     300

SWEETSORGHUM     301 AGATTGCTGAGCAACATTCTGACTTTGTGATGGGATTTATATCGGTAAAT     350
                     |||||||||||||||||||||||.|||||||||||||||||.||.|||||
SUGARCANE        301 AGATTGCTGAGCAACATTCTGATTTTGTGATGGGATTTATCTCAGTAAAT     350

SWEETSORGHUM     351 CCTGCATCCTGGTCAGTAACACCATCAAGCCCGGCGTTCATCCATGCCAC     400
                     ||||||||.||||||||||||||||||||||||||||||.||||||||||
SUGARCANE        351 CCTGCATCTTGGTCAGTAACACCATCAAGCCCGGCGTTTATCCATGCCAC     400

SWEETSORGHUM     401 ACCTGGAGTTCAGATGGTCGCTGGAGGAGATGATCTTGGGCAACAATACA     450
                     ||||||||||||||||||||||||||||||||||||||||||||||||||
SUGARCANE        401 ACCTGGAGTTCAGATGGTCGCTGGAGGAGATGATCTTGGGCAACAATACA     450

SWEETSORGHUM     451 ACACTCCTGAGTCTGTGGTAAACTACAGGGGCAGTGACATAATCATAGTT     500
                     |||||||||||||||||.|||||||||||||||||.||||||||||||||
SUGARCANE        451 ACACTCCTGAGTCTGTGATAAACTACAGGGGCAGCGACATAATCATAGTT     500

SWEETSORGHUM     501 GGACGTGGGATTATAAAGGCTAGCGACCCTATGAAGACGGCATGGGAGTA     550
                     |||||.||||||||||||||||||.|||||||||||||||||||||||||
SUGARCANE        501 GGACGCGGGATTATAAAGGCTAGCGATCCTATGAAGACGGCATGGGAGTA     550
```

Figure 21A

```
SWEETSORGHUM    551 CCGCTTGCAAGGGTGGCAGGCATACAAGAACAGCTTGCTATGAGAGGGGC  600
                    ||||||||||||||||||||||||||||||||||||||||||||| |||||
SUGARCANE       551 CCGCTTGCAAGGGTGGCAGGCATACAAGAACAGCTTGCTATGAG-GGGGC  599

SWEETSORGHUM    601 GTCGTGAGCATTCCAA--GGGCAAATCCAGGCGATTGGCGTAATAAGAGC  648
                    |.|||.|||||||||   |||||||||||.|||.||||||||||||||||
SUGARCANE       600 GCCGTAAGCATTCCAAGTGGGCAAATCCAAGCGTTTGGCGTAATAAGAGC  649

SWEETSORGHUM    649 ATACGGAAAGGTCTCCCTACAGTTGAGTCAGGACCTAATTGCAATCAGAC  698
                    ||.|||||||||.|||||||||||.|||||||||||||||||||||||||
SUGARCANE       650 ATGCGGAAAGGTCCCCCTACAGTCGAGTCAGGACCTAATTGCAATCAGAC  699

SWEETSORGHUM    699 TCACTGCAGAGGAGATTCATCCAGAGCATGCTTCATCATCGTTTGTGTTA  748
                    |||||||||||||||.||||||||||||||||.|||||||||||||||||
SUGARCANE       700 TCACTGCAGAGGAGACTCATCCAGAGCATGCTCCATCATCGTTTGTGTTA  749

SWEETSORGHUM    749 GAATAATTTCCTCTTGGTTCACACCGTTCGTGTTGGTCGAGTTATTAGGC  798
                    |||||||||||||||||||||.||||||.|||||||||||||   |||||
SUGARCANE       750 GAATAATTTCCTCTTGGTTCACTCCGTTCTTGTTGGTTGAG---TTAGGC  796

SWEETSORGHUM    799 ATTGTGATGCCTGTGTTGGGTTAGATCGTCTTATTGCCACTCTGGGTTAG  848
                    ||||||||||                     ||.|
SUGARCANE       797 ATTGTGATGC---------------------TGTC------------    810

SWEETSORGHUM    849 CTCCGGACTCCGAGCAATGTGATGCTTTTGATGCCGAAAATCCTATGACT  898
                                                   |||||||||    |||
SUGARCANE       811 -------------------------------GATGCCGAAA--------ACT  823

SWEETSORGHUM    899 CCACGCGTGCTTAGCTTGGCCTTCGCTTAATGCTTTTCACCTCCCAGTCT  948
                    ||.||.||||||||.|||  |.||||.|.|||||||||||
SUGARCANE       824 CCGCGTGTGCTTAACTT-GTCTTCACGTAATGCTTTTCA-----------  861

SWEETSORGHUM    949 CCCACTCCCAGTGCTTCTGTT           969
                             |||||||||||||.
SUGARCANE       862 -------CCAGTGCTTCTGTGGTGAC       880

METHOD OF MODIFYING THE CARBOHYDRATE CONTENT OF A PLANT

RELATED APPLICATION INFORMATION

This application is a 35 U.S.C. §371 national stage application of PCT Application No. PCT/IB2010/002331, filed Sep. 17, 2010, which claims priority from South African Patent Application No. 2009/06506, filed Sep. 17, 2009, the disclosures of which are incorporated by reference herein in their entireties.

FIELD OF THE INVENTION

This invention relates to a method of modifying at least one carbohydrate in a tissue of a plant, to a vector for use therefor, and to a transformed plant cell, plant part or transgenic plant containing the vector.

BACKGROUND TO THE INVENTION

Sucrose, harvested primarily from sugarcane, is both a major human food as well as an important feedstock for fuel ethanol production. The commercial production of sugar may therefore benefit by either increasing the sugar content of the crop or increasing cane yield. Since increasing the sugar content of sugarcane results in increased sugar yields with a relatively small increase in associated production costs, gains in sugar content are viewed as economically more beneficial than corresponding increases in cane yield. This means that increased sugar content has become an important objective of sugarcane breeding programs and transgenic research using biotechnology-based approaches.

Many biotechnology-based approaches for increasing the reduced carbon or nitrogen content of crops are directed towards increasing the concentrations of direct precursors of the target product (Sonnewald et al., 1997; Stark et al., 1992), These approaches tend to focus on increasing the concentration of the relevant metabolites, however have never resulted in significant increases of the target metabolite in a storage organ.

A need therefore exists for an alternative method of modifying the carbohydrate content of crops such as sugar cane, and for crops such as sugar cane with a relatively higher sugar content.

OBJECT OF THE INVENTION

It is an object of this invention to provide a method of modifying the content of at least one carbohydrate of a plant.

SUMMARY OF THE INVENTION

According to the invention, there is provided a method of increasing the content of at least one carbohydrate in one or more plant cells, the method including inhibiting UMP synthase (UMPS) activity in the one or more plant cells.

In some embodiments, the method of inhibiting UMPS activity will include the step of inserting into one or more plant cells at least one gene silencing cassette. Expressing the gene silencing cassette(s) thereby results in decreased UMP synthase activity and increased content of at least one carbohydrate (e.g. sucrose). Decreased UMPS activity may be brought about by various mechanisms (see e.g. discussion in the detailed description below regarding methods for reducing UMPS expression).

In some embodiments, the one or more gene silencing cassettes will be inserted into a population of cells (e.g. a callus).

In some embodiments, a transgenic plant is regenerated from one or more plant cells produced as described above. Plant tissue and plant parts (for example, seeds, storage organs etc.) may be harvested from the plant.

In some embodiments, plant tissue having an increased content of at least one carbohydrate is produced from one or more plant cells transformed as described above. This may optionally comprise regenerating a transgenic plant from one or more transformed plant cells. The term "tissue" is used herein in a broad sense and includes a reference to an aggregate of cells. The cells of the tissue may be differentiated or undifferentiated. In some embodiments the cells may have a similar structure and/or function. In some embodiments the cells may be specialized to perform a particular function. In one embodiment, the tissue is a callus.

In some embodiments, one or more plant cells are transformed with one or more gene silencing cassette(s) which include nucleic acid operably linked to one or more transcription elements for transcribing the nucleic acid wherein transcription of the nucleic acid decreases activity of UMP synthase.

Optionally the nucleic acid comprises (and optionally consists of) one or more of the following:
(i) the antisense sequence of a UMPS ORF (e.g. the nucleotide sequence of SEQ ID NO 1), or part thereof (e.g. at least 10, 15, 20, 25, 30, 40, 50, 70, 100, 150, 200, 300, 400, 500, 600, 700 nucleotides of the sequence),
(ii) a nucleotide sequence at least 80%, 85%, 90%, 95%, or 99% similar, to the antisense sequence of a UMPS ORF (e.g. SEQ ID NO 1), or to part thereof,
(iii) the sense sequence of a UMPS ORF (e.g. the nucleotide sequence of SEQ ID NO 2), or part thereof,
(iv) a nucleotide sequence at least 80%, 85%, 90%, 95%, or 99% similar, to the sense sequence of a UMPS ORF (e.g. SEQ ID NO 2), or to part thereof,
(v) (a) (i) or (ii) as above, and (b) (iii) or (iv) as above, optionally with a spliceable intron sequence between (a) and (b), and wherein the spliceable intron sequence is preferably at least 70 or 74 bp in length, preferably at least 100 bp, 200 bp, 300 bp, 400 bp, 450 bp, or 500 bp in length, and more preferably at least 74 bp in length.

In at least some embodiments, the UMPS ORF corresponds to the UMPS ORF of the transformed plant cell. Thus, for instance, where the plant cell is a sugarcane plant cell the UMPS ORF is the ORF of sugarcane and thus, for example, in accordance with (i) above, the nucleic acid comprises the antisense sequence of a sugarcane UMPS ORF, or part thereof.

In some embodiments, two or more gene silencing cassettes may be inserted into one or more plant cells, e.g. a first gene silencing cassette with nucleic acid according to (i) or (ii) above, and a second gene silencing cassette with nucleic acid according to (iii) or (iv) above. Thus, embodiments are envisaged wherein sense and antisense molecules are expressed from single or separate gene silencing cassettes. Such molecules may be used in double-stranded RNA interference whereby a sense and an antisense RNA molecule that is fully or partially complementary to the sense RNA molecule of a UMPS gene are expressed in the same plant cell, resulting in inhibition of the expression of the corresponding endogenous mRNA encoding UMPS.

In some embodiments, the one or more transcription elements include a promoter, optionally a monocotyledonous promoter (e.g. a UBI promoter).

In some embodiments, the at least one carbohydrate is selected from the group consisting of sucrose, starch, glucose, and fructose. In some embodiments, the method results in an increased content of both starch and sucrose and optionally one or more further carbohydrates (e.g. glucose).

In some embodiments, the plant is a sugar-storing plant, optionally selected from the group including sugarcane, sweet sorghum, and sugar beet. In some embodiments the plant is of the genus *Saccharum*, optionally sugarcane.

Plant cells, plant tissue, plants and plant parts (e.g. seeds, storage organs, sugar cane) obtained or obtainable by the method described above are included within the scope of the invention.

According to the invention there is further provided a vector comprising one or more gene silencing cassettes for decreasing UMPS activity in a plant cell.

In some embodiments the vector is a RNAi vector.

In some embodiments, the gene silencing cassette(s) include nucleic acid operably linked to one or more transcription elements for transcribing the nucleic acid wherein transcription of the nucleic acid decreases activity of UMPS.

Optionally the nucleic acid comprises (and optionally consists of) one or more of the following:
(i) the antisense sequence of a UMPS ORF (e.g. the nucleotide sequence of SEQ ID NO 1), or part thereof (e.g. at least 10, 15, 20, 25, 30, 40, 50, 70, 100, 150, 200, 300, 400, 500, 600, 700 nucleotides of the sequence),
(ii) a nucleotide sequence at least 80%, 85%, 90%, 95%, or 99% similar, to the antisense sequence of a UMPS ORF (e.g. SEQ ID NO 1), or to part thereof,
(iii) the sense sequence of a UMPS ORF (e.g. the nucleotide sequence of SEQ ID NO 2), or part thereof,
(iv) a nucleotide sequence at least 80%, 85%, 90%, 95%, or 99% similar, to the sense sequence of a UMPS ORF (e.g. SEQ ID NO 2), or to part thereof,
(v) (a) (i) or (ii) as above, and (b) (iii) or (iv) as above, optionally with a spliceable intron sequence between (a) and (b), and wherein the spliceable intron sequence is preferably at least 70 or 74 bp in length, preferably at least 100 bp, 200 bp, 300 bp, 400 bp, 450 bp, or 500 bp in length, and more preferably at least 74 bp in length.

In some embodiments, the one or more transcription elements include a promoter, optionally a monocotyledonous promoter (e.g. a UBI promoter).

In some embodiments, the at least one carbohydrate is selected from the group consisting of sucrose, starch, glucose, and fructose. In some embodiments, the method results in an increased content of both starch and sucrose and optionally one or more further carbohydrates (e.g. glucose).

In some embodiments, the plant is a sugar-storing plant, optionally selected from the group including sugarcane, sweet sorghum, and sugar beet. In some embodiments the plant is of the genus *Saccharum*, optionally sugarcane.

According to the invention there is also provided a transformed plant cell which includes a vector comprising one or more gene silencing cassettes for decreasing the activity of UMPS in a plant cell.

In some embodiments the vector is a RNAi vector.

In some embodiments, the gene silencing cassette(s) include nucleic acid operably linked to one or more transcription elements for transcribing the nucleic acid wherein transcription of the nucleic acid decreases activity of UMPS.

Optionally the nucleic acid comprises (and optionally consists of) one or more of the following:
(i) the antisense sequence of a UMPS ORF (e.g. the nucleotide sequence of SEQ ID NO 1), or part thereof (e.g. at least 10, 15, 20, 25, 30, 40, 50, 70, 100, 150, 200, 300, 400, 500, 600, 700 nucleotides of the sequence),
(ii) a nucleotide sequence at least 80%, 85%, 90%, 95%, or 99% similar, to the antisense sequence of a UMPS ORF (e.g. SEQ ID NO 1), or to part thereof,
(iii) the sense sequence of a UMPS ORF (e.g. the nucleotide sequence of SEQ ID NO 2), or part thereof,
(iv) a nucleotide sequence at least 80%, 85%, 90%, 95%, or 99% similar, to the sense sequence of a UMPS ORF (e.g. SEQ ID NO 2), or to part thereof,
(v) (a) (i) or (ii) as above, and (b) (iii) or (iv) as above, optionally with a spliceable intron sequence between (a) and (b), and wherein the spliceable intron sequence is preferably at least 70 or 74 bp in length, preferably at least 100 bp, 200 bp, 300 bp, 400 bp, 450 bp, or 500 bp in length, and more preferably at least 74 bp in length.

In some embodiments, the one or more transcription elements include a promoter, optionally a monocotyledonous promoter (e.g. a UBI promoter).

In some embodiments, the at least one carbohydrate is selected from the group consisting of sucrose, starch, glucose, and fructose. In some embodiments, the method results in an increased content of both starch and sucrose and optionally one or more further carbohydrates (e.g. glucose).

In some embodiments, the plant is a sugar-storing plant, optionally selected from the group including sugarcane, sweet sorghum, and sugar beet. In some embodiments the plant is of the genus *Saccharum*, optionally sugarcane.

According to the invention there is further provided a transgenic plant, plant part or plant tissue containing or derived from a transformed plant cell which includes a vector comprising one or more gene silencing cassettes for decreasing the activity of UMPS in a plant cell.

In some embodiments the vector is a RNAi vector.

In some embodiments, the gene silencing cassette(s) include nucleic acid operably linked to one or more transcription elements for transcribing the nucleic acid wherein transcription of the nucleic acid decreases activity of UMPS.

Optionally the nucleic acid comprises (and optionally consists of) one or more of the following:
(i) the antisense sequence of a UMPS ORF (e.g. the nucleotide sequence of SEQ ID NO 1), or part thereof (e.g. at least 10, 15, 20, 25, 30, 40, 50, 70, 100, 150, 200, 300, 400, 500, 600, 700 nucleotides of the sequence),
(ii) a nucleotide sequence at least 80%, 85%, 90%, 95%, or 99% similar, to the antisense sequence of a UMPS ORF (e.g. SEQ ID NO 1), or to part thereof,
(iii) the sense sequence of a UMPS ORF (e.g. the nucleotide sequence of SEQ ID NO 2), or part thereof,
(iv) a nucleotide sequence at least 80%, 85%, 90%, 95%, or 99% similar, to the sense sequence of a UMPS ORF (e.g. SEQ ID NO 2), or to part thereof,
(v) (a) (i) or (ii) as above, and (b) (iii) or (iv) as above, optionally with a spliceable intron sequence between (a) and (b), and wherein the spliceable intron sequence is preferably at least 70 or 74 bp in length, preferably at least 100 bp, 200 bp, 300 bp, 400 bp, 450 bp, or 500 bp in length, and more preferably at least 74 bp in length.

In some embodiments, the one or more transcription elements include a promoter, optionally a monocotyledonous promoter (e.g. a UBI promoter).

In some embodiments, the at least one carbohydrate is selected from the group consisting of sucrose, starch, glucose, and fructose. In some embodiments, the method results in an increased content of both starch and sucrose and optionally one or more further carbohydrates (e.g. glucose).

In some embodiments, the plant is a sugar-storing plant, optionally selected from the group including sugarcane, sweet sorghum, and sugar beet. In some embodiments the plant is of the genus *Saccharum*, optionally sugarcane.

In some embodiments, the plant is of the genus *Saccharum*, optionally sugarcane, and the transgenic plant part a callus.

The term "carbohydrate" as used herein refers to energy-producing organic compounds such as starches and sugars.

The term "UMP Synthase" as used herein refers to an enzyme capable of catalyzing the final two steps of de novo pyrimidine biosynthesis and having both orotate phosphoribosyl transferase and orotidylate decarboxylase activity.

BRIEF DESCRIPTION OF THE DRAWINGS

One embodiment of the invention will be described, by way of example only, with reference to the drawings in which:

FIG. 20 shows BLAST search output for sequences producing significant alignments using the sugarcane UMPS DNA sequence TC68130;

FIG. 21 shows a pairwise sequence alignment of the sugarcane UMPS DNA sequence TC68130 (sugarcane) and sweet sorghum UMPS DNA sequence (XM_002456891.1) (sweet sorghum); and SEQ ID NO 1 shows the antisense sequence of the UMPS ORF, and SEQ ID NO 2 shows the sense sequence of the UMPS ORF.

DETAILED DESCRIPTION WITH REFERENCE TO THE DRAWINGS

Figure 1:
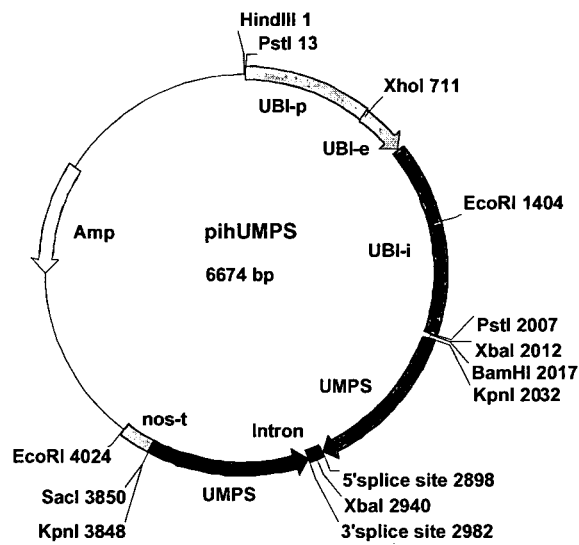
FIG. 1 is a schematic representation of the plant expression vector, pihUMPS, containing the 801 bp UMPS cDNA fragment in both sense and antisense orientation and separated by a 74 bp intron.

The preparation of a transgenic plant usually includes transforming a cell of a plant known as a protoplast. Transformation techniques for dicotyledons are well known in the art and include *Agrobacterium*-based techniques and techniques which do not require *Agrobacterium*.

Transformation techniques include transformation via particle bombardment, protoplast uptake, such as with PEG and by electroporation, and microinjection. The choice of vector depends largely on the preferred selection for the species being transformed. A whole transgenic plant may then be generated from the transformed protoplast using standard techniques.

*Agrobacterium*-mediated transformation is a technique used for transformation of dicotyledons because of its high efficiency of transformation and its broad utility with many different species which include tobacco, tomato, sunflower, cotton, oilseed rape, potato, soybean, alfalfa and poplar. *Agrobacterium* transformation typically involves the transfer of a binary vector, carrying the exogenous DNA, to an appropriate *Agrobacterium* strain. The strain selected depends on the complement of vir genes carried by the host *Agrobacterium* strain either on a co-resident plasmid or chromosomally. The transfer of the recombinant binary vector, to *Agrobacterium* is carried out by triparental mating using *E. coli* transformed with the recombinant binary vector. The recombinant binary vector can also be transferred to *Agrobacterium* by DNA transformation. Transformed tissue is regenerated on a selectable medium carrying an antibiotic or herbicide resistance marker.

Direct gene transfer into protoplasts using PEG or electroporation techniques and particle bombardment into callus tissue are preferred transformation techniques for monocots. Transformation can be carried out with a single vector or with multiple vectors. Transformation of rice can also be undertaken by direct gene transfer techniques utilizing protoplasts or particle bombardment. Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells.

Methods for preparing nucleic acids encoding nucleotide sequences to effect gene silencing are known in the art. For instance, cDNA encoding the nucleic acid is inserted into a plant transformation vector in the form of a cassette containing all of the necessary elements for transformation of the plant cell and expression of the cDNA to produce the nucleic acid in the plant cell. The cassette may, for example, contain in proper reading frame and therefore operably linked, a promoter functional in plant cells, a 5' non-translated leader sequence, the insert DNA, and a 3' non-translated region functional in plants to cause the addition of polyadenylated nucleotides to the 3' end of the RNA sequence for translational requirements.

Promoters for expression of nucleic acids in plant cells, and the nucleotide sequence thereof, may, for example, originate from plants or plant DNA viruses, and various promoters for this purpose are used in the art. Selected promoters may have constitutive activity such as the CaMV 35S promoter, the actin promoter, and the ubiquitin promoter. Alternatively, they may be inducible and thus drive the expression of the resistance gene at the sites of wounding or pathogen infection. Other useful promoters are expressed in specific cell types (such as leaf epidermal cells, meosphyll cells, root cortex cells) or in specific tissues or organs (roots, leaves or flowers, for example), such as the maize trpA gene that is preferentially expressed in pith cells and the promoter derived from the maize gene encoding phosphoenolpyruvate carboxylase (PEPC) which directs expression in a leaf-specific manner. The selected promoter may drive expression of the gene under a light induced or other temporally regulated promoter. A further alternative is that the selected promoter be chemically regulated. The promoter may also be specific for expression of the nucleic acid in monocotyledonous plants or for dicotyledonous plants.

A variety of transcriptional cleavage and polyadenylation sites are available for use in expression cassettes. These are responsible for correct processing (formation) of the 3' end of mRNAs. Appropriate transcriptional cleavage and polyadenylation sites functional in plants include the CaMV 35S cleavage and polyadenylation sites, the tml cleavage and polyadenylations sites, the nopaline synthase cleavage and polyadenylation sites, the pea rbcS E9 cleavage and polyadenylation sites. These can be used in both monocotyledons and dicotyledons.

A number of non-translated leader sequences derived from viruses are known to enhance expression, specifically in dicotyledonous cells. Leader sequences from Tobacco Mosaic Virus (TMV, the "Ω-sequence"), Maize Chlorotic mottle Virus (MCMV), and Alfalfa Mosaic Virus (AMV) may be used to enhance expression.

An expression cassette comprising nucleic acid containing one or more of the various elements described above may be inserted into a plant transformation vector by standard recombinant DNA methods. Alternatively, some or all of the elements of the expression cassette may be present in the vector, and any remaining elements may be added to the vector as necessary. Many transformation vectors are commercially available for plant transformation, and the nucleic acids of this invention can be used in conjunction with any such vectors. Most vectors include one or more genes encoding selection marker proteins. The vector used will depend upon the preferred transformation technique, the target species for transformation, and the selection marker desired. For certain target species, specific antibiotic or herbicide selection markers may be preferred, such as the nptll gene which confers resistance to kanamycin, the bar gene which confers resistance to the herbicide phosphinothricin, the hph gene which confers resistance to the antibiotic hygromycin, and the dhfr gene, which confers resistance to methotrexate.

In accordance with the invention, transgenic plants may be prepared using standard techniques which result in down-regulation or upregulation in expression of a gene or complete obliteration of its expression. In this way, plant cells, plants, plant parts etc. may be produced with reduced UMPS activity. The change in expression may be caused by the introduction of sequences which interfere with gene expression. Such sequences are known in the art and include antisense constructs, sense constructs, RNA silencing constructs, or RNA interference molecules; or it may be caused by genomic disruptions of the sensitivity gene itself through the use of, for example, transposons, tilling, homologous recombination, or nonsense mutations. The use of antisense nucleic acids is well known in the art, and can be RNA, DNA, a PNA or any other appropriate molecule. Catalytic RNA molecules or ribozymes can be used to inhibit expression of sensitivity genes. Ribozymes may be designed that specifically pair with target RNA and cleave the phosphodiester backbone at a specific location, thereby functionally inactivating the target RNA. Ribozyme sequences may be used in combination with antisense RNAs. Transgenic plants which include one or more inactivated sensitivity genes can also be produced by using RNA silencing or interference (RNAi), which can also be termed post-transcriptional gene silencing (PTGS) or cosuppression.

In the context of this invention, "gene silencing" (also called RNA silencing, RNAi or RNA-mediated interference) includes a reference to any mechanism through which the presence of a single-stranded or double-stranded RNA in a cell results in the inhibition of expression of a target gene which comprises a sequence identical or nearly identical to that of the RNA, and includes, but is not limited to: RNA interference, repression of translation of a target mRNA transcribed from the target gene without alteration of the mRNA's stability, and transcriptional silencing such as by histone acetylation and heterochromatin formation leading to inhibition of transcription of the target mRNA.

Any method to reduce the expression of a UMP synthase gene in a plant can be used in the practice of the invention. The term "expression" as used herein in the context of a gene product refers to the biosynthesis of that gene product, including the transcription and/or translation and/or assembly of the gene product. Methods for silencing (i.e. reducing or eliminating) the expression of a gene in a plant are well known in the art, and any such method may be used in the methods of the present invention. Antisense constructions, fully or partly complementary to at least a portion of the messenger RNA (mRNA) for the target sequence can be utilized as mentioned above. Antisense nucleotides are designed to bind to the corresponding mRNA.

Modifications of the sequences for use in UMP gene silencing molecules of the invention may be made as long as the sequences bind to, and interfere with, expression of the corresponding mRNA. In this regard, sequences having at least about 70%, at least about 80%, at least about 85%, at least about 90%, at least about 95%, at least about 99%, or higher sequence similarity to the target UMP sequence may be used with the invention. Parts of the sequences for use in UMP gene silencing molecules of the invention may be also used to disrupt the expression of the target UMP gene. The use of sequences of at least about 10 nucleotides, at least about 20 nucleotides, at least about 30 nucleotides, at least about 40 nucleotides, at least about 50 nucleotides, at least about 100 nucleotides, at least about 200 nucleotides, at least about 300, at least about 400, at least about 450, at least about 500, at least about 550, or greater may preferably be used. Cosuppression may also be used to inhibit the expression of the target UMP gene. In this regard, a heterologous UMP synthase sequence may be expressed in the sense orientation to inhibit expression of the endogenous UMP synthase gene.

Sequences similar to the UMP gene described herein may be found using various publically available databases known in the art such as GenBank (http://www.ncbi.nlm.nih.gov/Genbank/index.html).

The use of spliceable intron sequences in regulating the expression of exogenous genes in transgenic plants are known in the art. Spliceable intron sequences of at least 70 nt may be used with the invention. The use of sequences of at least about 70 nucleotides, at least about 100 nucleotides, at least about 200 nucleotides, at least about 300, at least about 400, at least about 450, at least about 500, at least about 550, or greater art known in the art. Spliceable intron sequences of up to about 0.75 kb or even up to 1.1 kb in length are known in the art.

In one embodiment of the invention the sucrose, starch and glucose content of transgenic sugarcane tissue is increased by the RNAi-based down-regulation of UMPS. Briefly, a vector containing a gene silencing cassette is inserted into a plant cell, the gene silencing cassette including nucleic acid having the nucleotide sequence of SEQ ID NO 1 and SEQ ID NO 2 and a spliceable 74 bp intron sequence there between, the gene silencing cassette operably linked to a transcription element in the form of the monocotyledonous promoter: the UBI promoter. Transcription of the nucleic acid in the plant cell decreases activity of UMP synthase. A transgenic sugarcane plant is then regenerated from the transformed plant cell; and sugarcane tissue with increased carbohydrate content is produced.

EXAMPLE

1. Introduction

Although uridine nucleotides have been reported by various groups to be important cofactors in the use of sugars for starch synthesis, recent work by Geigenberger et al. (2005) demonstrated that antisense inhibition of the de novo pathway of pyrimidine synthesis results in a compensatory stimulation of the lower energy-consuming salvage pathways. Downstream effects of the inhibition of this pathway in potato tubers included an elevated uridine nucleotide pool, elevated starch contents, decreased sucrose contents and an improved crop yield.

De novo pyrimidine nucleotide biosynthesis, also referred to as the orotate pathway, is defined as the formation of UMP from carbamoylphosphate (CP), aspartate, and 5-phosphoribosyl-1-pyrophosphate (PRPP). Pyrimidine nucleotide biosynthesis consists of six enzymatic steps. Carbamoylphosphate synthase (CPSase) produces CP from a combination of carbonate, ATP, and an amino group. CP is used not only in pyrimidine de novo synthesis, but also as a precursor for arginine biosynthesis. The next step, in which aspartate transcarbamoylase (ATCase) catalyzes the condensation of CP with aspartate to form carbamoylaspartate (CA), is specific for pyrimidine biosynthesis. Cyclization of the carbamoylaspartate to produce the pyrimidine ring is catalyzed by the enzyme dihydroorotase (DHOase). Subsequently, dihydroorotate (DHO) is oxidized by dihydroorotate dehydrogenase (DHODH) to yield orotate (OA). Orotate is condensed with PRPP to orotidine 5-monophosphate (OMP) by orotate phosphoribosyltransferase (OPRTase), which is then decarboxylated by orotidylate decarboxylase (ODCase) to form uridine-5-monophosphate (UMP).

As de novo synthesis of nucleotides is energy consuming, cells have developed a strategy to reuse preformed nucleosides and nucleobases through salvage reactions. The nucleosides uridine/cytidine and thymidine are salvaged to their respective nucleotides by specific nucleoside kinases and uracil is directly salvaged with PRPP into UMP via uracil phosphoribosyltransferase. Salvage pathways may also play an important role in providing nucleobases to cells, which are unable to synthesize sufficient amounts for their needs.

In plants, UMP synthase is a bifunctional protein catalyzing the final two steps of de novo pyrimidine biosynthesis. As in higher eukaryotes, plant UMP synthase has both orotate phosphoribosyl transferase (OPRTase, EC 2.4.2.10) and orotidylate decarboxylase (ODCase, EC 4.1.1.23) activities.

Inhibition of UMP synthase by antisense inhibition of the de novo pathway of pyrimidine synthesis has previously been shown to result in decreased sucrose contents (Geigenberger et al., 2005). In contrast, we report herein the unexpected increase in sugar content of a plant as a result of antisense inhibition of the de novo pathway of pyrimidine synthesis.

2. Materials and Methods

All chemicals were obtained from Sigma-Aldrich (South Africa) unless otherwise indicated. All coupling enzymes were obtained from Roche (South Africa) unless otherwise indicated.

2.1 Preparation of Transgenic Sugarcane Plants 2.1.1 Cloning of the UPMS Silencing Vector pihUMPS The ihpRNA vector used in this project was based on high-throughput RNAi gene silencing technology. The pihUMPS vector (FIG. 1) was constructed from a 801 bp PCR product amplified from full length sugarcane UMPS cDNA cloned into pGEM®-T Easy (Promega). UMP synthase cDNA was isolated from sugarcane (variety N19) leaf roll RNA. Specific Forward (GCAAGTTTGCTGACATTGGA) and Reverse (CCACAGAAGCACTGGTGAAA) primers were designed from DNA sequence of sugarcane obtained from TIGR (TC68130, www.tigr.org) using Primer3 software (frodo.wi.mit.edu). The isolated sequences show open reading frames (ORFs) of 166 amino acids. Because of the multi-cloning site availability as well as the T7 primer and the reverse T3; the pGEMT-Easy vector was used to clone the isolated gene prior to sub-cloning into pBlueScript® SK and pBlueScript® KS (using the Pstl and Apal sites) modified to contain a 45 bp intron sequences. The inserts and their adjacent intron segments from the modified pBlueScript® SK and pBlueScript® KS were subsequently isolated (following digestion of the plasmids with Kpnl and Xbal). The expression vector pU3Z (which contains a monocotyledonous promoter) was likewise digested with Kpnl and dephosphorylated. Using two-insert ligation, the pihUMPS construct was constructed which included the sense and antisense strands of UMP synthase. The UMPS gene fragments were separated by a fully assembled intron of 74 nucleotides in length. The pihUMPS vector therefore contained a UMPS fragment in antisense and sense orientation on either side of a spliceable intron sequence and operably linked to the UBI promoter.

2.1.2 Plant Material

Sugarcane plants (transgenic and wild type *Saccharum* spp. variety N19) were grown under greenhouse conditions ($\approx$16 h light period, $\approx$25° C.). Three ripe stalks of each selected transgenic line were harvested. To limit metabolite losses, plant tissues (internodes 8-10 pooled) were cut into liquid $N_2$ directly after harvest and ground to a fine powder in an IKA® A11 basic (IKA) analytical mill. All tissues were stored in 50 mL screw cap tubes (Corning) at $-80°$ C.

2.1.3 Plant Transformation

The pihUMPS vector was used to co-transform sugarcane calli using standard protocols. Transgenic calli were selected using Genetycin according to standard protocols, based on the npt-II selection marker in the co-transformed construct, and regenerated into plants. Regenerated plants were hardened off and grown under greenhouse conditions for further analysis.

2.1.4 PCR Screening of Putative Transformants

To select positively transformed clones, transformants were screened by means of PCR amplification for the presence of the pihUMPS vector. DNA was extracted from 30-50 mg tissues from mature internodes (8-10) of putative transgenic lines as described by a method modified from McGarvey and Kaper (1991). 400 µL extraction buffer (50 mM Tris-HCl, pH 8.0, 1% cetyltrimethylammonium bromide (CTAB) (Merck), 0.7 M NaCl, 10 mM EDTA, 0.5% polyvinylpirrolidone, 0.1% β-mercaptoethanol (BME, added just before use)) was added to the tissue and vortexed for 1 minute. Tubes were then incubated for 60 min at 60° C. 400 µL chloroform was added and samples were vortexed and spin down (13 000 rpm, 5 min). The aqueous layer was transferred to new Eppendorff tubes containing 1 volume cold 100% isopropanol and incubated on ice for 15 min. The precipitated nucleic acids was spun down (13 000 rpm, 10 min) and washed in 70% EtOH, dried and resuspended in 20 µL TE-buffer (10 mM Tris-HCl, pH 7.5, 1 mM EDTA) containing 20 µg/mL RNaseA. The PCR reaction included 25 ng template DNA, Intron Forward (GAT CCC ACC TGC ATCGAT; 10 µM), Nos-t (AAG ACC GGC AAC AGG ATT C; 10 µM), 10 µM dNTPs (1 µM each), 10×PCR buffer containing 0.37 mM $MgCl_2$, and 0.25 µL Taq polymerase enzyme (1 U) to a final volume of 25 µl. The cycling parameters included incubation of the PCR reaction for 3 mins at 94° C., followed by a 3-step cycle of 94° C. for 30 secs, 60° C. for 45 secs and 72° C. for 2 mins, repeated a total of 30 times. A final elongation step of 5 mins at 72° C. was included.

For each transformation seven independent regenerated plants that were resistant to geneticin were transferred to soil and hardened off under standard conditions.

2.2 Characterisation of Gene Expression 2.2.1 Semi-quantitative Gene Expression Analysis of Endogenous UMP Synthase and NDPase Using RT-PCR Suspension cells (tissue culture) as well as internodes (8-10) tissue collected from greenhouse grown mature plants were used for RNA extraction. Total RNA was extracted from all tissues according to a modified method of Bugos et al. (1995). Tissues were cut into small pieces directly into liquid N2 and ground in an IKA® A11 basic analytical mill. The fine powder was transferred to a 50 ml sterile tubes (Corning) in liquid N2 and stored at $-80°$ C. Two grams frozen tissue was added to 10 mL homogenisation buffer (0.1 M Tris, pH 8.0, 1 mM EDTA, 0.1 M NaCl, 1% SDS (w/v), 0.1% BME) and 10 mL phenol:chloroform (1:1) in a 50 mL tube and vortexed. Sodium acetate, pH 5.2, was added to a final concentration of 0.1 M and the emulsion was incubated on ice for 15 min followed by centrifugation at 4° C. (12 000 g, 15 min). The aqueous phase was transferred to a new tube containing 3 volumes 100% EtOH and 0.1 volume 3 M sodium acetate, pH 5.2, mixed and precipitated at $-20°$ C. for two hours. The precipitated nucleic acid was spun down at 4° C. (12000 g, 15 min) and washed in 75% EtOH. Samples were resuspended in water and treated with Deoxyribonuclease I (RNase-free, Fermentas) according to the manufacturer's instructions followed by precipitation in 2.5 volumes 100% EtOH, 0.1 volume sodium acetate.

Semi-quantitative RT-PCR was used to determine whether down-regulation of UMP synthase transcription resulted in up-regulation of transcripts coding for salvage enzymes such as NDPase. Five pg total RNA obtained from mature internode tissues of transgenic sugarcane showing reduced UMP synthase activity was reverse transcribed using the RevertAid™ First Strand cDNA Synthesis Kit (Fermentas, USA) according to manufacturer's instructions. The primers used for amplifying UMPS RNA transcripts were: forward (GCT-TGAAGCTGAAGGGTTTG) and reverse (ACACAAAC-GATGATGGAGCA); for nucleoside diphosphate phosphatase (NDPase) were: forward (AAGGCCTTGAAGCTTGTGAA) and reverse (TGCAAA-GACGCGAAAGTAAA); and for the housekeeping actin gene were: forward (ACTGGGACGACATGGAGAAG) and reverse (TTCTCCACAGAGGAGCTGGT). Each PCR reaction contained 0.5 µg cDNA as template. RT-PCR amplification of the housekeeping gene α-Actin was carried out to normalize the amount of template cDNA.

Five transgenic sugarcane lines were selected for further analysis based on UMP synthase activity level and regeneration plant availability. These transgenic sugarcane lines were labelled 2.2, 3.1, 3.2, 3.3, and 4.2, and are referred to as such hereafter. In further analyses, the transgenic sugarcane lines were compared to the non-transformed or wild-type sugarcane (WT).

2.3 Characterisation of Enzyme Activity 2.3.1 Protein Determination

Protein concentrations was determined according to Bradford (1976) using a commercially available protein assay solution (Bio-Rad) according to manufacturer's instructions. Bovine Albumin (Fraction V) (Roche) was used as protein standard.

2.3.2 Assay for UMP Synthase (UMPS), Uridine Kinase (UK), and Uracil Phosphoribotransferase (UPRTase) Activity Crude protein extracts were made from Callus/suspension culture and maturing internodal tissue (8-10). The protein extraction buffer consisted of 50 mM HEPES-NaOH, pH 7.6, 2 mM EDTA, 10% glycerol, 28 mM β-mercaptoethanol, 2% PVPP and Complete which was added just prior to use. Extracts were incubated on ice for 10 minutes and spun down for 15 min (10 000×g, 4° C.). Supernatants were transferred to Sephadex G-50 (Sigma-Aldrich) spin columns pre-equilibrated in extraction buffer and spun down for 2 min (10000 rpm, 4° C.). UMP Synthase reaction was initiated by adding the desalted protein in the assay cocktail containing, 50mM HEPES-NaOH (pH 7.6), 10mM $MgCl_2$, 2mM $MgCl_2$ 28 μM β-mercaptoethanol, 0.6 mM PRPP, 45 μM Labelled [2-$^{14}$C] Orotic Acid. The reaction mixture was incubated for 15-25 min at room temperature and stopped by boiling for 2 minutes; modified from Ashihara et al. 2000. Two (2) μl was load in a TLC and run for 1 h in a buffer butanol: acetic acid: water (25:24:1).

For Uridine Kinase (UK), the reaction was initiated by adding the desalted protein in the assay cocktail containing, 50 mM HEPES-NaOH (pH 7.6), 10 mM $MgCl_2$ 2 mM $MgCl_2$ 28 μM β-mercaptoethanol, 3.75 mM ATP, 45 μM Labelled [2-$^{14}$C] Uridine. The reaction mixture was incubated for 15-25 min at room temperature and stopped by boiling for 2 minutes; modified from Ashihara et al. 2000. Two (2) μl was load in a TLC and run for 1 h in a buffer containing butanol: acetic acid: water (25:24:1).

For Uracil phosphoribotransferase (UPRTase), the reaction was initiated by adding the desalted protein in the assay cocktail containing, 50 mM HEPES-NaOH (pH 7.6), 10 mM $MgCl_2$, 2 mM $MgCl_2$ 28 μM β-mercaptoethanol, 0.6 mM PRPP, 45 μM Labelled [2-$^{14}$C] Uracil. The reaction mixture was incubated for 15-25 min at room temperature and stopped by boiling for 2 minutes; modified from Ashihara et al. 2000. Two (2) μl was load in a TLC and run for 1 h in a buffer butanol: acetic acid: water (25:24:1).

2.3.3 Sucrose, Hexose and Starch Extraction and Quantification

Fifty milligrams (50±10 mg) frozen tissue were added to 500 μL 80% ethanol. Suspensions were incubated at 65° C. overnight and spun down for 5 min (3500×g, RT). The supernatant was used directly for the sugar assay. Residues were re-extracted one more times in 80% ethanol and the supernatants were discarded to remove remaining hexoses. The pellets were resuspended in 500 μl MilliQ $H_2O$ and incubated at 100° C. for 4 h. Supernatants were either used directly for starch background analysis or stored at −20° C. The pellets were resuspended in 100 μL buffer (50 mM NaCL) containing 10 units AMG and incubated at 55° C. for 2 h.

Enzymatic quantification was performed according to the method of Bergmeyer and Bernt (1974). For hexose analysis, 5 μL extract was added to 45 μL MilliQ $H_2O$ and 200 μL buffer A (150 mM Tris pH 8.1, 5 mM $MgCl_2$, 1 mM ATP (Roche), 1 mM NADP (Roche)) in a 96 well microtitre plate (Nunc). Following an initial reading at $A_{340}$, 0.5 U of Hexokinase/Glucose 6-phosphate dehydrogenase (HK/G6-PDH) was added and incubated for 30 min at RT. A second reading was taken to calculate the free glucose content. 0.7 U of Phosphoglucose isomerase (PGI) was added and incubated for 30 min at RT. A third reading was taken to calculate the free fructose content present in the extract. To quantify the sucrose present in the sample, 5 μL of the extract was incubated with 40 μL buffer B (100 mM Citrate pH 5.0, 5 mM $MgCl_2$) and 10 U β-Fructosidase (Roche) for 15 min at RT. Following the addition of 200 μL buffer A and 0.5 U HK/G6-PDH, samples were incubated and read as before. All spectrophotometric readings were obtained using a PowerWaveX plate reader.

2.3.4 Assay for Sucrose Phosphate Synthase (SPS) Activity

SPS activity was determined in callus and Internodes (8-10) tissues. SPS activity was assayed according to Baxter et al. (2003) under maximal ($V_{max}$) and limiting ($V_{lim}$) reaction conditions. The protein extraction buffer consisted of 50 mM HEPES-KOH, pH 7.5, 10 mM $MgCl_2$, 1 mM EDTA, 10 mM DTT and Complete® (Roche) protease inhibitor cocktail tablets which was added just prior to use according to the manufacturers instructions. Extracts were spun down for 2 min (16 000 g, 4° C.). Supernatants were transferred to Sephadex G-25 (Sigma-Aldrich) spin columns pre-equilibrated in extraction buffer and spun down for 2 min (2000 rpm, 4° C.). 100 μL crude protein sample was incubated for 30 min at 35° C. with 100 μL assay buffer (50 mM HEPES-KOH, pH 7.5, 20 mM KCl and 4 mM $MgCl_2$) containing (a) $V_{max}$ assay; 12 mM UDP-Glc, 10 mM Fruc 6-P and 40 mM Glc-6-P, or (b) $V_{lim}$, assay; 4 mM UDP-Glc, 2 mM Fru-6-P, 8 mM Glc-6-P and 5 mM $KH_2PO_4$. The reaction was heated to 95° C. for 5 min to stop the reaction and spun down at 16 000 g for 5 min. 100 μL supernatant was added to 100 μL of 5 M KOH and incubated at 95° C. for 10 min to destroy unreacted hexose phosphates. After adding 200 μL anthrone reagent (0.14% anthrone in 14.6 M $H_2SO_4$) to 50 μL sample, absorbance was measured at 620 nm in a PowerWaveX spectrophotometer. The absolute amount of sucrose was calculated from a standard curve with 0-200 nmol sucrose.

2.3.5 Assay for Sucrose Synthase (SuSy) in the Sucrose Breakdown Direction

To determine the rate of sucrose breakdown in callus and Internodes (8-10) tissues, the catalytic activity of SuSy was assayed according to Schäfer et al (2004). The protein extraction buffer consisted of 100 mM Tris-HCl, pH 7.0, 10 mM $MgCl_2$, 1 mM EDTA, 10 mM DTT and Complete® (Roche) protease inhibitor cocktail tablets which was added just prior to use according to the manufacturers instructions. Extracts were spun down for 2 min (16 000 g, 4° C.). Supernatants were transferred to Sephadex G-25 (Sigma-Aldrich) spin columns pre-equilibrated in extraction buffer and spun down for 2 min (2000 rpm, 4° C.). Crude protein samples (20 μL) were incubated with assay buffer consisting of 100 mM Tris-HCl (pH 7.0), 2 mM $MgCl_2$, 400 mM sucrose, 2 mM $NAD^+$, 1 mM sodium pyrophosphate, 4 U/mL Phosphoglucomutase (Roche), 4 U/mL Glucose-6-phosphate dehydrogenase (Roche). Reactions were started by the addition of uridine diphosphate (UDP) to 2 mM. NADH production was monitored at 340 nm.

2.3.6 Assay for Sucrose Synthase (SuSy) in the Sucrose Synthesis Direction

To determine the rate of sucrose synthesis in callus and Internodes (8-10) tissues, the synthetic activity of SuSy was assayed according to Schäfer et al (2004). The protein extraction buffer consisted of 100 mM Tris-HCl, pH 7.0, 10 mM $MgCl_2$, 1 mM EDTA, 10 mM DTT and Complete® (Roche) protease inhibitor cocktail tablets. Extracts were spun down for 2 min (16 000 g, 4° C.). Supernatants were transferred to Sephadex G-25 (Sigma-Aldrich) spin columns pre-equilibrated in extraction buffer and spun down for 2 min (2000 rpm, 4° C.). Crude protein samples (20 μL) were incubated with assay buffer consisting of 100 mM Tris-HCl (pH 7.5), 15 mM $MgCl_2$, 20 mM UDP-glucose, 0.2 mM NADH, 1 mM phosphoenolpyruvate (PEP) and 0.45 U/mL Pyruvate kinase/Lactate dehydrogenase (PK/LDH, Roche). Reactions were started by the addition of fructose to 10 mM. $NAD^+$ production was monitored at 340 nm.

2.3.7 Assay for ADP-Glucose Pyrophosphorylase Activity

ADP-glucose pyrophosphorylase activity was assayed according to a modify method from Ou-Lee and Setter (1985). Assay cocktail consisted of 50 mM HEPES buffer (pH 7) containing 5 mm $MgCl_2$, 5 mM ADP-glucose, 2 mM Sodium Pyrophosphate (PPi), 1 mM NADP+, 4 U/mL phosphoglucomutase, 4 U/mL 6-phosphogluconate dehydrogenase and 4 U/mL glucose-6-phosphate dehydrogenase. The background reading was done for 5 minutes at 340 nm after adding 20 μL of proteins extract in the assay cocktail without PPi, and the reaction initiated by adding PPi and read for 20 minutes at 340 nm.

2.3.8 Assay for UDP-Glucose Pyrophosphorylase Activity

UDP-glucose pyrophosphorylase activity was assayed according to a modify method from Ou-Lee and Setter (1985). Assay cocktail consisted of 100mM Tris buffer (pH 7) containing 2 mm $MgCl_2$, 10 mM UDP-glucose, 1 mM Sodium Pyrophosphate (PPi), 1 mM NAD+, 4 U/mL phosphoglucomutase, and 4 U/mL glucose-6-phosphate dehydrogenase. The background reading was done for 5 minutes at 340 nm after adding 20 μL of protein extract in the assay cocktail without PPi, and the reaction initiated by adding PPi and read for 20 minutes at 340 nm.

2.3.9 Sucrose, Hexose and Starch Extraction and Enzymatic Quantification

Fifty milligrams (50 ±10 mg) frozen tissue were added to 500μL 80% ethanol. Suspensions were incubated at 65° C. overnight and spun down for 5 min (3500×g, RT). The supernatant was directly use for sugar assay. Residues were re-extracted one more time in 80% ethanol and the supernatants were discarded to remove remaining hexoses. The pellets were resuspended in 500 μl MilliQ $H_2O$ and incubated at 100° C. for 4 h. Supernatants were either used directly for starch background analysis or stored at −20° C. The pellets were resuspended in 100 μL buffer (50 mM NaCL) containing 10 units AMG and incubated at 55° C. for 2 h. Enzymatic quantification was performed according to the method of Bergmeyer and Bernt (1974).

For hexose analysis, 5 μL extract was added to 45 μL MilliQ H2O and 200 μL buffer A (150 mM Tris pH 8.1, 5 mM MgCl2, 1 mM ATP (Roche), 1 mM NADP (Roche)) in a 96 well microtitre plate (Nunc). Following an initial reading at 340 nm, 0.5 unit of Hexokinase/Glucose 6-phosphate dehydrogenase (HK/G6-PDH) was added and incubated for 30 min at room temperature. A second reading was taken to calculate the free glucose content. 0.7 unit of Phosphoglucose isomerase (PGI) was added and incubated for 30 min at room temperature. A third reading was taken to calculate the free fructose content present in the extract. To quantify the sucrose present in the sample, 5 μL of the extract was incubated with 40 μL buffer B (100 mM Citrate pH 5.0, 5 mM MgCl2) and 10 units β-Fructosidase (Roche) for 15 min at room temperature. Following the addition of 200 μL buffer A and 0.5 unit HK/G6-PDH, samples were incubated and read as before. All spectrophotometric readings were performed using a PowerWaveX plate reader.

2.3.10 Hexose Phosphate and Nucleotide Determination

Metabolite extractions were performed according to Stitt et al. (1989). One gram of previously stored tissues was added to 1.5 mL ice cold 10% HClO4, vortexed and incubated at 4° C. for 20 minutes with mixing. Insoluble material was spun down for 2 minutes (13 000 rpm, at 4° C.). Following removal of the supernatant, the pellet was washed and incubated for 15 minutes with 500 μL 2% HClO4, spun down for 2 minutes (13 000 rpm, 4° C.), and pooled with the first supernatant. Samples were neutralized (pH 7.0-7.5) by the addition of 5M KOH, 1M triethanolamine and incubated at 4° C. for 15 minutes. The insoluble KClO4 was spun down for 2 minutes (13 000 rpm) and the neutralized supernatant was filtered in a 0.25 μm and used for hexose phosphate quantification. The filtered neutralized supernatant was flash-freeze in liquid nitrogen and freeze dried in a Speed Vac Plus SC11A.

For hexose phosphates assay, 20 μL of sample was added to 230 μL reaction buffer containing 100 mM Tris, pH 8.0, 5 mM MgCl2 and 0.25 mM NADP in a 96-well plate. The background was read at 340 nm. 0.7 unit G6-PDH, 0.7 unit PGI and 0.2 unit phosphoglucomutase (PGM) in 5 mM Tris-HCl, pH 8.0 were added sequentially, incubated for 15 minutes at room temperature and read at 340 nm to determine glucose-6-phosphate, fructose-6-phosphate and glucose-1-phosphate respectively. Nucleotides and nucleotide sugars were assayed from the resuspended freeze dried samples using high pressure liquid chromatography.

2.3.11 Statistical Analysis of Data

The Student's t-test was used to test for significant differences between group means. The square of the Pearson product moment correlation coefficient (coefficient of determination) was calculated to indicate correlation between characteristics. STATISTICA (data analysis software system), version 8. www.statsoft.com) was used for all statistical analysis.

2.3.10 Bioinformatic Analysis of Sugarcane UMPS

The DNA sequence of sugarcane UMPS (TC68130) was used to carry out a BLAST search for highly similar DNA sequences using the online tools available at blast.ncbi.nlm-.nih.gov/Blast.cgi. The regions sequences showing high similarity were each aligned to the sugarcane UMPS DNA using standard web based alignment tools such as that offered by the EMBL-European Bioinformatics Institute and available online at www.ebi.ac.uk/Tools/emboss/align/index.html.

3 Results

3.1 Confirmation of Putative Transgenic Sugarcane Lines

Figure 2:
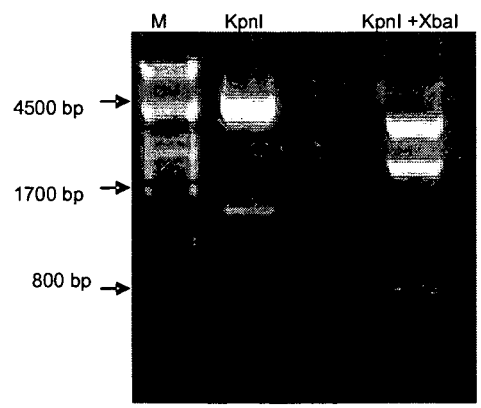
FIG. 2 is an agarose gel showing the resolved restricted products of a Kpnl and Xbal pihUMPS digestion.

The identity of pihUMPS (as shown in the plasmid map of FIG. 1) was confirmed by restriction enzyme digestion using Kpnl and Xbal and resolution of the restricted products by agarose gel electrophoresis. Kpnl digestion yielded the expected 4858 bp and 1816 bp fragments, while Kpnl and Xbal double-digestion yielded the expected 4838 bp, and 908 bp fragments (FIG. 2).

Figure 3:
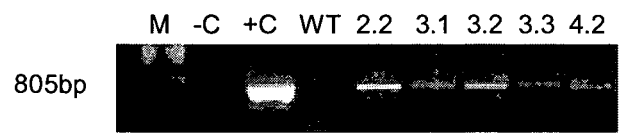
FIG. 3 is an agarose gel showing resolved PCR amplification products obtained during PCR screening of putative pihUMPS transformed sugarcane clones.

To select positively transformed clones, transformants were screened by means of PCR for the presence of the silencing vector (FIG. 3). DNA was extracted from mature internodes (8-10). For each transformation seven (7) independent regenerated plants that were resistant to geneticin were transferred to soil and hardened off under standard conditions. Five lines were selected for further analysis based on UMPS activity level and regeneration plant availability.

3.2 Characterisation of Gene Expression

Figure 4:
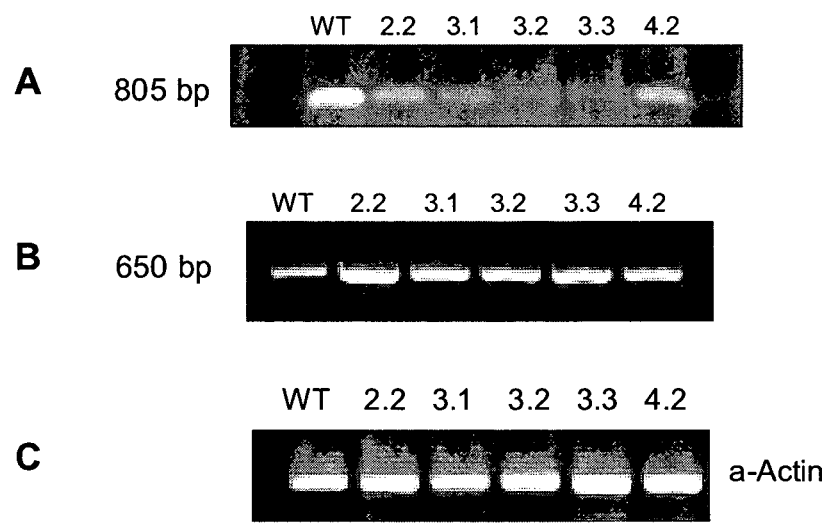
FIG. 4 is an agarose gel showing resolved RT-PCR amplification products obtained during semi-quantitative RT-PCR analysis of endogenous UMP Synthase (UMPS) expression (A), endogenous nucleoside diphosphate phosphatise (NDPase) expression (B), and endogenous actin expression (C) in transgenic clones.

3.2.1 Semi-quantitative Gene Expression Analysis of Endogenous UMP Aynthase (UMPS) and Nucleoside Diphosphate Phosphatase (NDPase) using RT-PCR Down-stream effects of UMPS silencing were expected to include a low transcription level of UMPS and up-regulation of the salvage pathway compared to that of the untransformed wild-type line. Semi-quantitative RT-PCR was therefore used to determine whether down-regulation of UMPS transcription resulted in up-regulation of transcripts coding for salvage enzymes such as NDPase. UMPS expression in mature internode tissues of transgenic sugarcane was observed to be less than that observed in the untransformed wild-type line (FIG. 4A), while NDPase expression was observed to be greater (FIG. 4B). The expression of the housekeeping gene α-Actin was similar in the transgenic sugarcane lines and in the untransformed wild-type line, confirming similar amounts of template cDNA were included in the RT-PCR reactions.

3.3 Characterisation of Enzyme Activity

3.3.1 Enzyme Activity of UMPS Synthase, UK, and UPRTase

Figure 5:
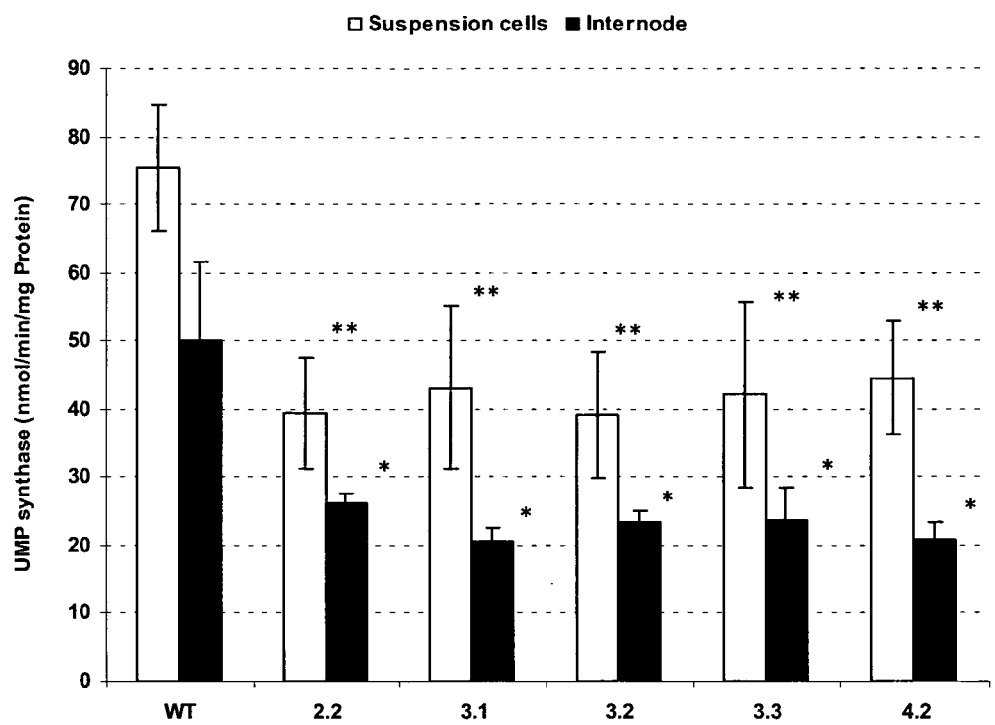
FIG. 5 shows repression of UMPS activity in sugarcane transformed with pihUMPS. Crude desalted protein extracts from the suspension cells and internodes 8-10 (Internode) were used to determine UMPS activity. Values calculated as mean±STDEV, n=3. *P≤0.02; **P≤0.002.
Figure 6:
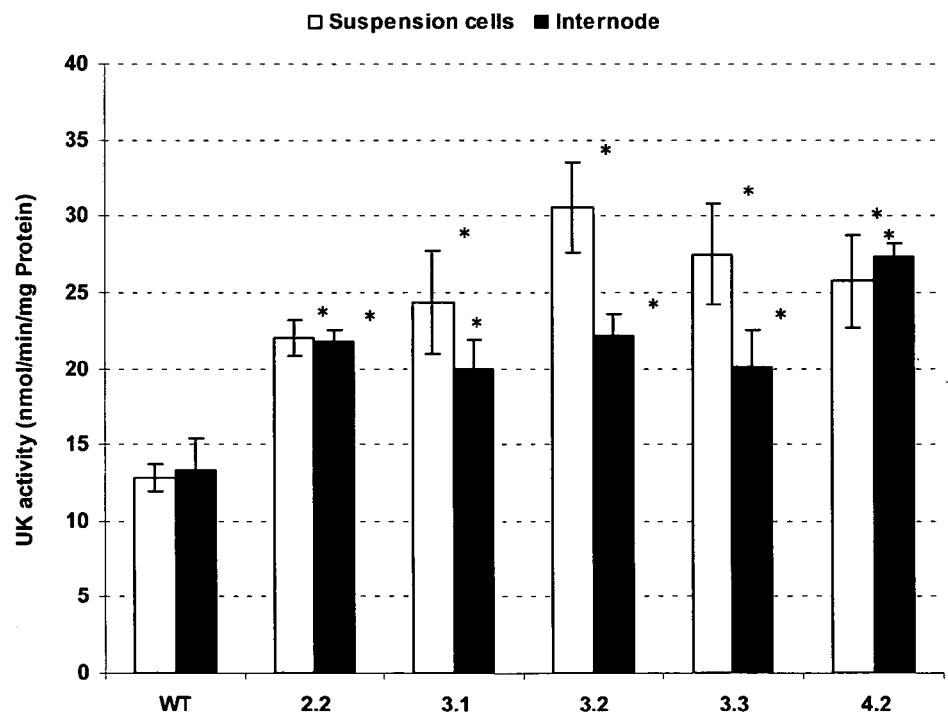
FIG. 6 shows up-regulation of uridine kinase (UK) activity in sugarcane transformed with pihUMPS. Crude desalted protein extracts from the suspension cells and internodes 8-10 (Internode) were used to determine UK activity. Values calculated as mean±STDEV, n=3. *P≤0.02.
Figure 7:
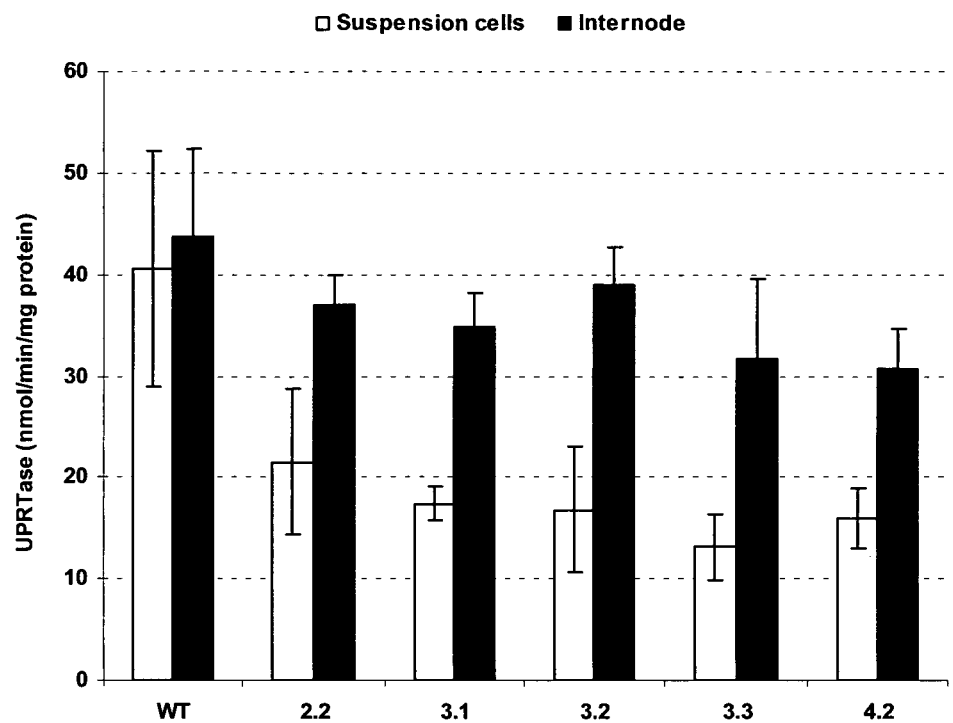
FIG. 7 shows uracil phosphoribosyltransferase (UPRTase) activity in sugarcane transformed with pihUMPS. Crude desalted protein extracts from the suspension cells and internodes 8-10 (Internode) were used to determine UPRTase activity. Values calculated as mean±STDEV, n=3. *P≤0.03.

Both suspension cells and internodal tissue obtained from all five transgenic sugarcane lines demonstrated significantly less UMPS activity than suspension cells and internodal tissue obtained from the wild-type sugarcane (FIG. 5), demonstrating successful RNAi-based targeting of UMPS expression. In contrast, enzyme activity of the salvage pathway enzyme UK was found to be significantly higher in suspension cells and internodal tissue obtained from all five transgenic sugarcane lines than that obtained from the wild-type sugarcane line (FIG. 6), demonstrating an up-regulation of the pyrimidine salvage pathway. UPRTase activity of suspension cells and internodal tissue obtained from all five transgenic sugarcane lines was generally less than that obtained from the wild-type sugarcane, with suspension cells from transgenic sugarcane lines 3.1, 3.2, 3.3, and 4.2 showing significantly less UPRTase activity (FIG. 7).

3.3.2 Enzyme Activity of Sucrose Synthase (SuSy)

Figure 8:
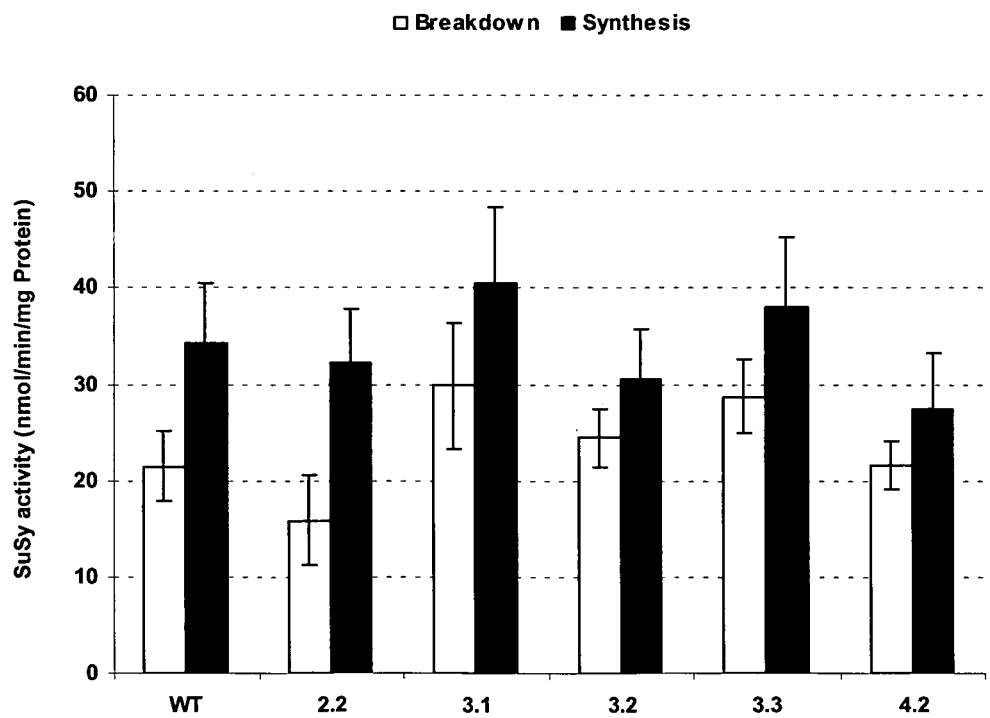
FIG. 8 shows Sucrose Synthase (SuSy) activity in both breakdown and synthesis in sugarcane transformed with pihUMPS. Crude desalted protein extracts from the suspension cells were used to determine SPS activity. Values calculated as mean±STDEV, n=3. *P≤50.03.

Crude desalted protein extracts from suspension cells and internodes 8-10 obtained from transgenic cell lines were analysed to determine SuSy activity. SuSy activity analysed in the breakdown direction was observed to be generally increased in suspension cells obtained from transgenic sugarcane lines 3.1, 3.2, and 3.3 and generally decreased in transgenic sugarcane lines 2.2, and 4.2 (FIG. 8). SuSy activity analysed in the synthesis direction was observed to be generally increased in suspension cells obtained from transgenic sugarcane lines 3.1 and 3.3 and generally decreased in transgenic sugarcane lines 2.2, 3.2, and 4.2 (FIG. 8).

Figure 9:
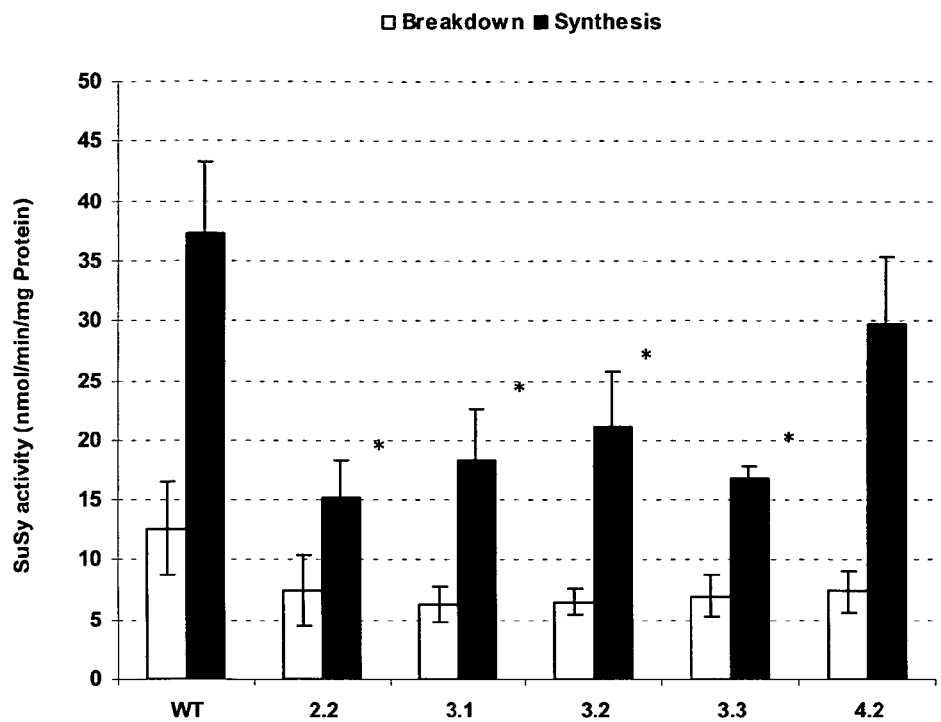
FIG. 9 shows Sucrose Synthase (SuSy) activity in both breakdown and synthesis in sugarcane transformed with pihUMPS. Crude desalted protein extracts from the internodes 8-10 were used to determine SPS activity. Values calculated as mean±STDEV, n=3. *P≤50.03.

However, SuSy activity analysed in both the breakdown and synthesis directions was observed to be significantly decreased in internodal tissue obtained from all the transgenic sugarcane (FIG. 9).

SuSy activity of suspension cells and internodal tissue of the transgenic sugarcane lines was assessed under maximal ($V_{max}$) and limiting ($V_{lim}$) conditions and compared to that of the untransformed wild-type line. The SuSy $V_{max}$ of suspension cells from transgenic sugarcane lines 3.1 and 3.2 was significantly greater than that of the untransformed wild-type line (Table 1). Furthermore, both the $V_{max}$ and the $V_{lim}$ of all the transgenic cell lines were significantly greater than that observed for the untransformed wild-type line (Table 1).

TABLE 1

Sucrose synthase (SuSy) activity in suspension cells and internodes obtained from transgenic sugarcane cell lines under maximal ($V_{max}$) and limiting ($V_{lim}$) conditions. Activity expressed in μmol/min/mg protein of standard deviation of means, n = 3.

| Lines | Suspension cells | | |
|---|---|---|---|
| | Vmax | Vlim | Vlim/Vmax |
| WT | 87.49 ± 5.23 | 64.84 ± 6.22 | 74.1 |
| 2.2 | 92.71 ± 3.55 | 65.61 ± 3.29 | 70.7 |
| 3.1 | 116.60 ± 3.75* | 70.54 ± 4.09 | 60.5 |
| 3.2 | 106.44 ± 6.21* | 70.41 ± 1.36 | 66.1 |
| 3.3 | 95.45 ± 1.66 | 52.83 ± 3.83 | 55.3 |
| 4.2 | 98.09 ± 7.94 | 71.04 ± 4.81 | 43.6 |
| Lines | Internodes | | |
| | Vmax | Vlim | Vlim/Vmax |
| WT | 8.81 ± 0.75 | 5.00 ± 0.38 | 56.8 |
| 2.2 | 14.93 ± 1.98* | 7.31 ± 0.85* | 48.9 |
| 3.1 | 13.20 ± 1.19* | 8.34 ± 1.76* | 63.2 |
| 3.2 | 13.52 ± 0.87* | 8.33 ± 1.47* | 61.65 |
| 3.3 | 16.33 ± 1.76* | 12.86 ± 1.53* | 78.8 |
| 4.2 | 14.35 ± 2.00* | 8.24 ± 1.19* | 57.5 |

3.3.3 Enzyme Activity of AGPase and UGPase

Figure 10:
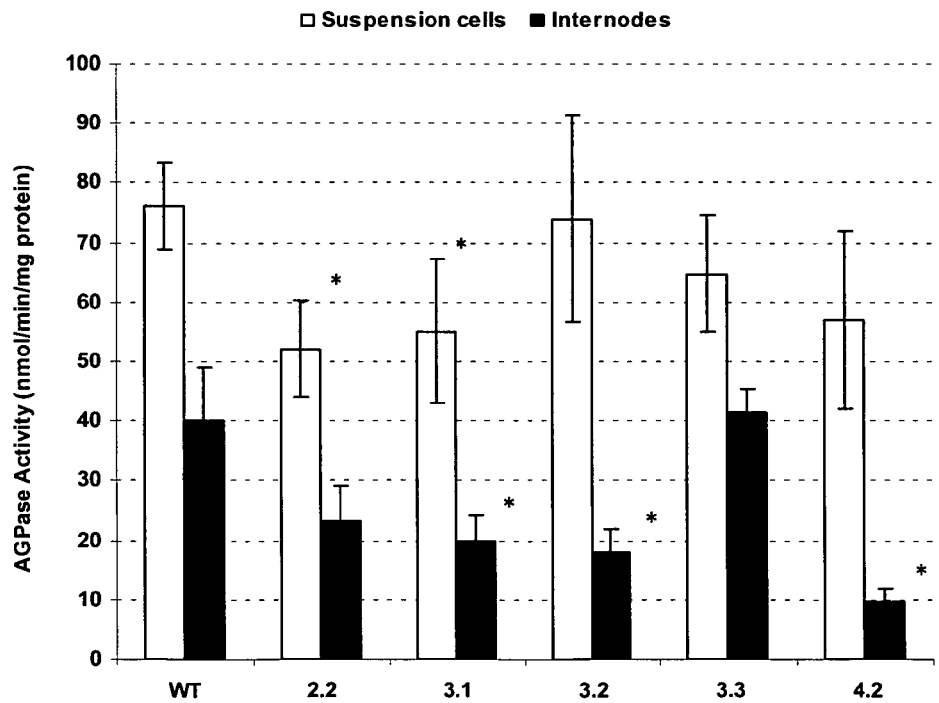
FIG. 10 shows ADP-glucose pyrophosphorylase (AGPase) activity in sugarcane transformed with pihUMPS. Crude desalted protein extracts from the suspension cells and internodes 8-10 (Internode) were used to determine AGPase activity. Values calculated as mean±STDEV, n=3. *P≤50.03.

Suspension cells obtained from transgenic sugarcane lines 2.2 and 3.1 demonstrated significantly less AGPase activity than suspension cells obtained from the wild-type sugarcane, while internodal tissue obtained from transgenic sugarcane lines 3.1, 3.2 and 4.2 demonstrated significantly less AGPase activity (FIG. 10).

Figure 11:
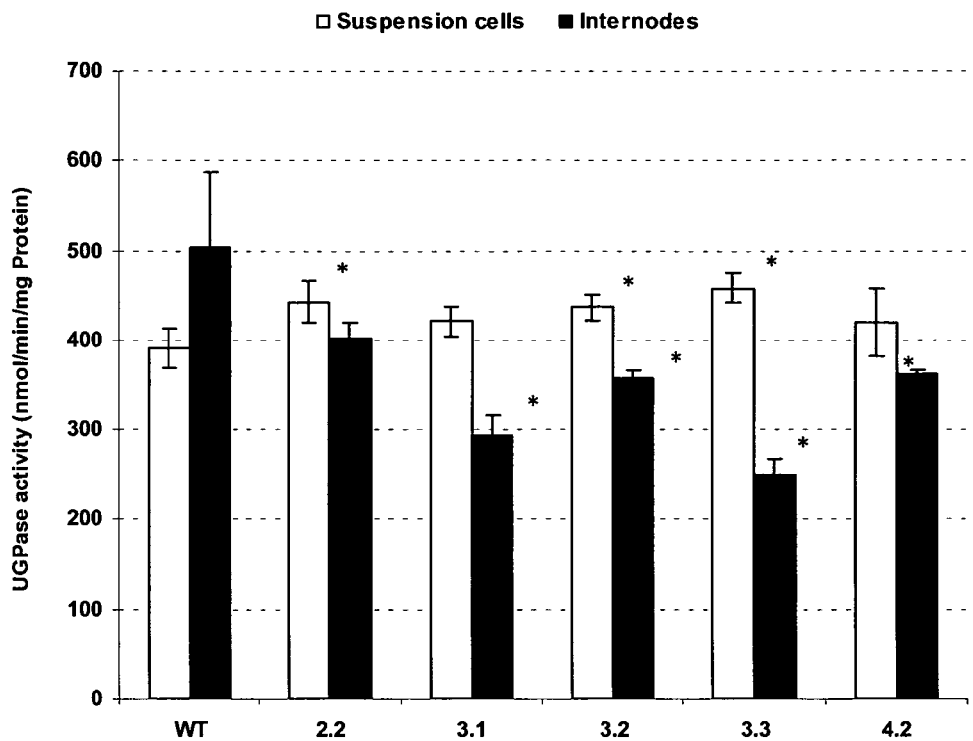
FIG. 11 shows UDP-glucose pyrophosphorylase (UGPase) activity in sugarcane transformed with pihUMPS. Crude desalted protein extracts from the suspension cells and internodes 8-10 (Internode) were used to determine UGPase activity. Values calculated as mean±STDEV, n=3. *P≤50.05.

Suspension cells obtained from transgenic sugarcane lines 2.2, 3.2, and 3.3 demonstrated significantly more UGPase activity than suspension cells obtained from the wild-type sugarcane, while internodal tissue obtained from transgenic sugarcane lines 3.1, 3.2, 3.3, and 4.2 demonstrated significantly less UGPase activity (FIG. 11).

Figure 12:
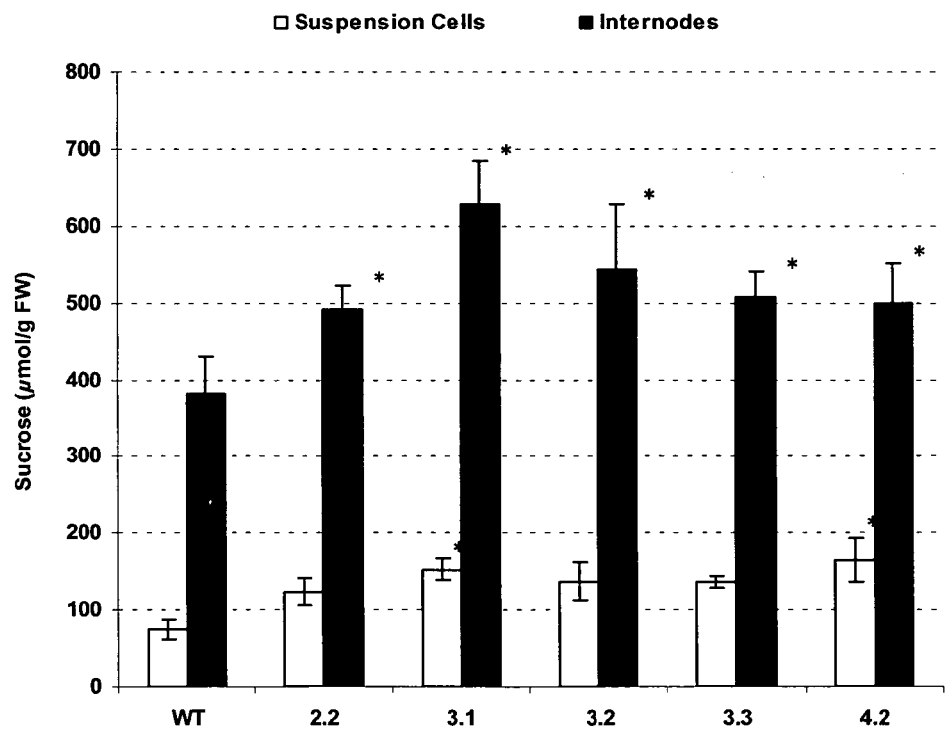
FIG. 12 shows sucrose content in sugarcane transformed with pihUMPS. Ethanol soluble extracts from the suspension cells and internodes 8-10 (Internode) were used to determine sucrose concentration. Values calculated as mean±STDEV, WT, n=5 and the transgenic sugarcane lines, n=3. *P≤5.0.05, *P≤50.02.
Figure 13:
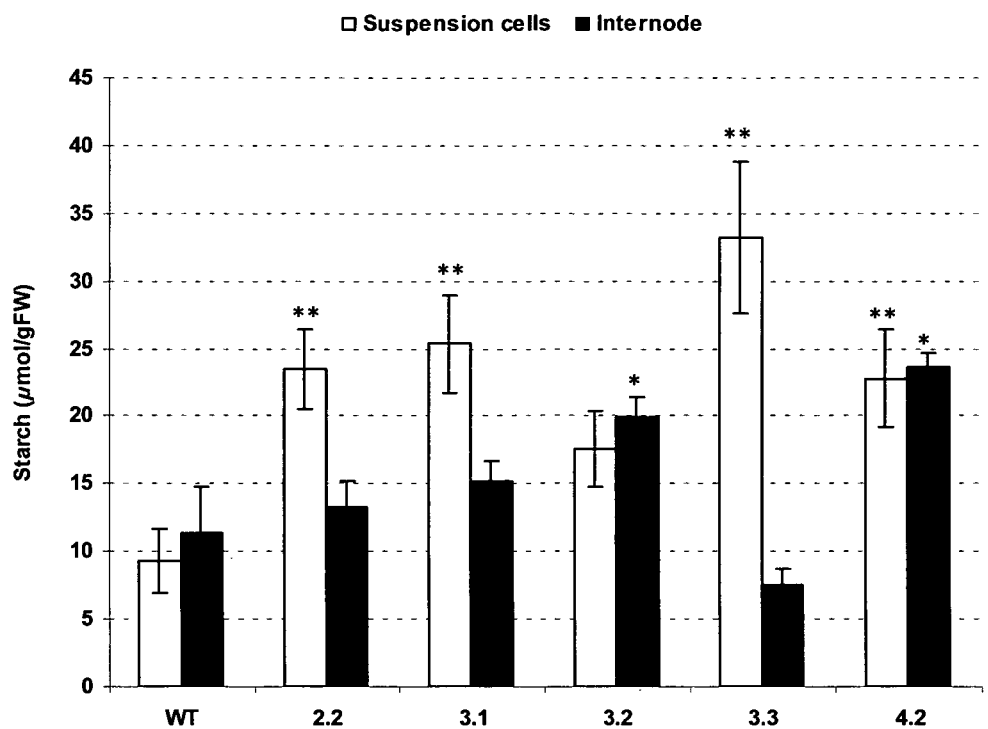
FIG. 13 shows starch content in sugarcane transformed with pihUMPS. Values calculated as mean±STDEV, WT, n=5 and the transgenic sugarcane lines, n=3. *P≤0.05, *P≤0.02.

3.3.4 Sucrose, Hexose and Starch Accumulation in Transgenic Sugarcane Lines The effect of RNAi-based targeting of UMPS expression on the accumulation of sucrose, glucose, fructose and starch in transgenic sugarcane, metabolites was assessed. The sucrose content of all transgenic sugarcane lines was observed to be significantly greater than that observed in the untransformed wild-type line in both suspension cells and intermodal tissue (FIG. 12), and starch content was significantly increased in suspension cells from all transgenic sugarcane lines (FIG. 13). Starch content in intermodal tissue obtained from transgenic sugarcane lines 3.2 and 4.2 was also observed to be significantly greater than the untransformed wild-type line (FIG. 13).

Figure 14:
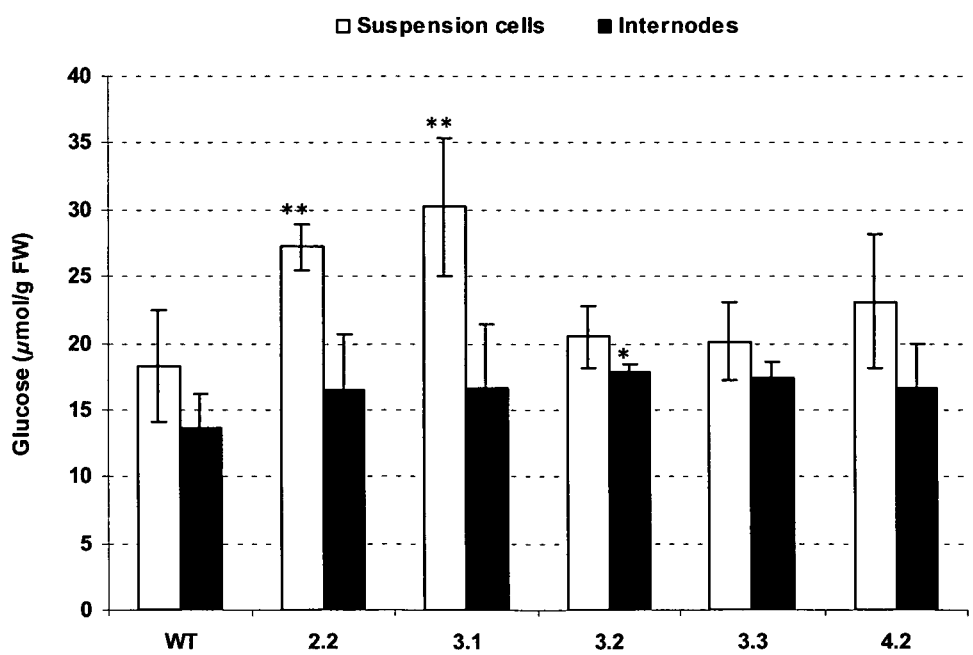
FIG. 14 shows glucose content in sugarcane transformed with pihUMPS. Values calculated as mean±STDEV, WT, n=5 and the transgenic sugarcane lines, n=3. *P≤0.05 *P≤0.02.
Figure 15:
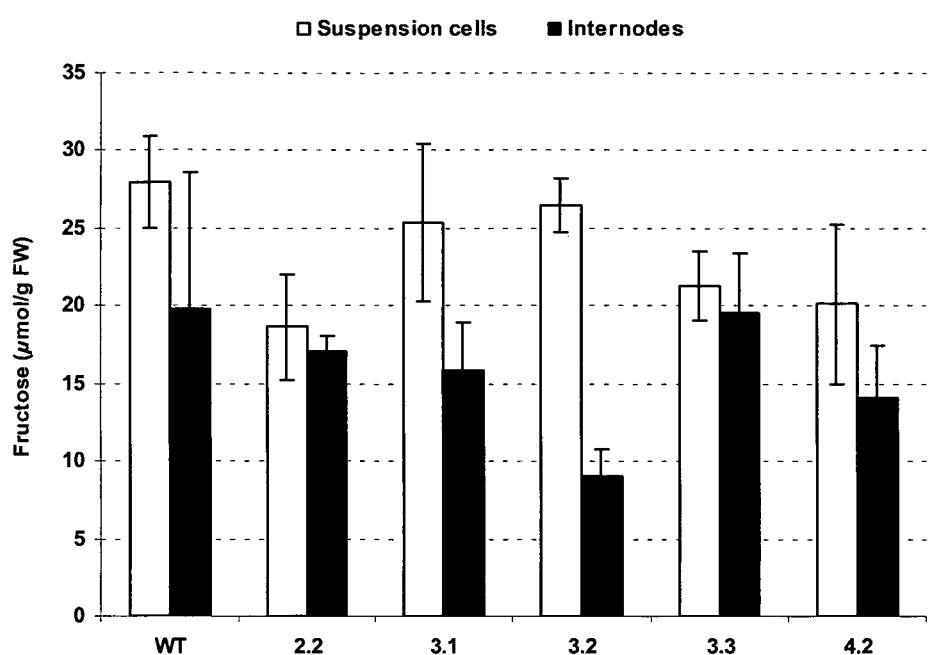
FIG. 15 shows fructose content in sugarcane transformed with pihUMPS. Values calculated as mean±STDEV, WT, n=5 and the transgenic sugarcane lines, n=3. *P≤0.05, *P≤0.02.

Glucose and fructose content of the transgenic sugarcane lines was also assessed and the glucose content was observed to be significantly increased in the suspension cells from clones 2.2 and 3.1, and in the internodal tissue of clone 3.2 (FIG. 14). Fructose content however not observed to be significantly different between the transgenic sugarcane lines and the untransformed wild-type line (FIG. 15).

3.3.5 Metabolites Analysis Using Linear Correlation

Figure 16:
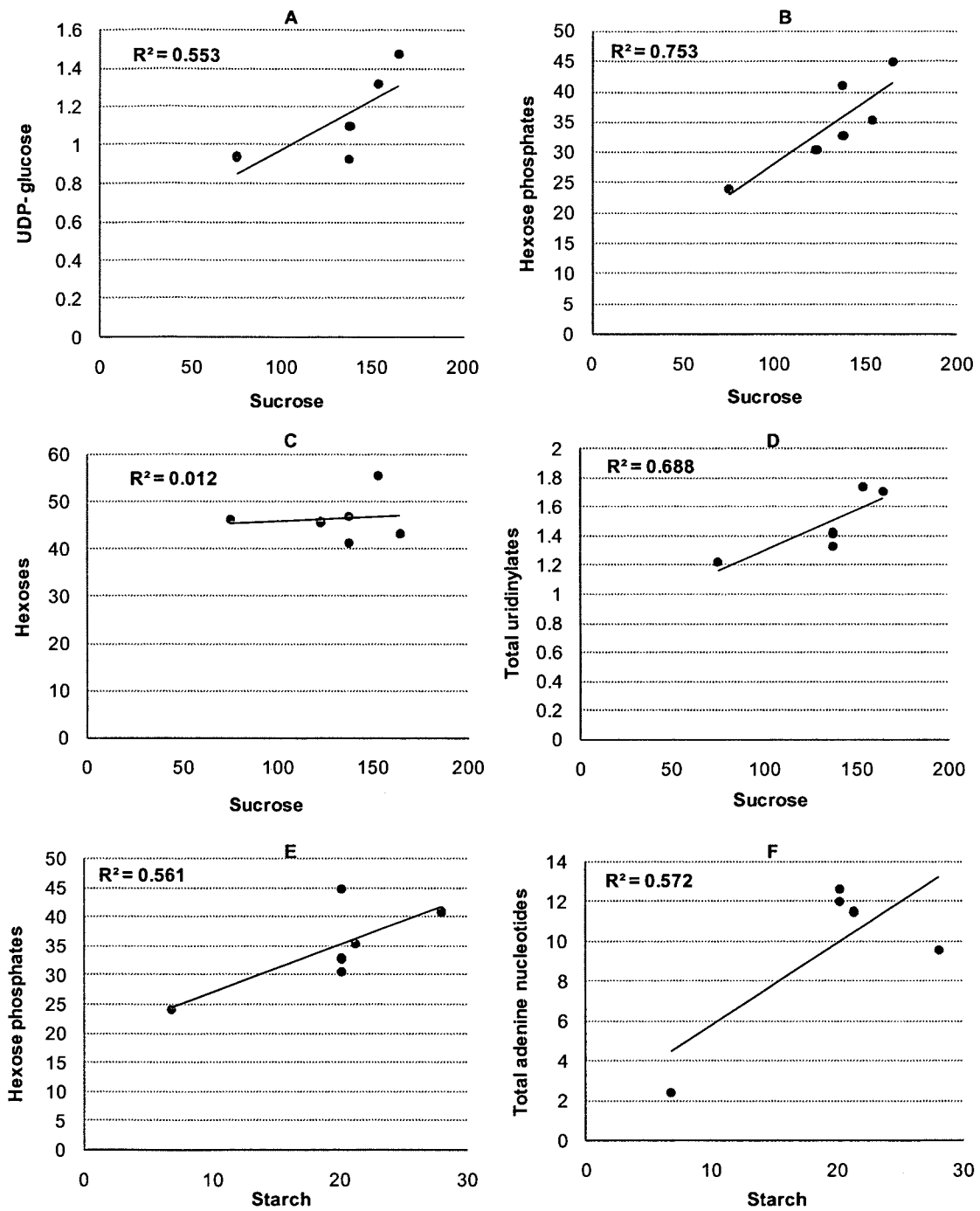
FIG. 16 shows linear correlations of metabolites involved in sucrose and starch metabolism in suspension cells. Apart from sucrose, starch and hexoses (μmol/g FW) all metabolite levels are given in nmol/g FW. For sucrose, (A) UDP-glucose, (B) hexose phosphates, (C) hexoses, (D) total uridinylates; for starch, (E) hexose phosphates, and (F) total adenine nucleotides. Data are mean of three independent suspension cultures per line.

Sucrose and starch contents were plotted against key metabolites to determine a possible relationship in both the suspension cells and the internodes. In the suspension cells, UDP-glucose, hexose phosphates and total uridinylates (UDP and UDP-glucose) positively correlated with increase in sucrose content in all transgenic lines with the strongest positive correlation ($R2=0.68$) observed between sucrose and both hexose phosphate and total uridinylates (FIGS. 16 B and D, respectively). No significant correlation was observed between sucrose and hexoses, however, changes in starch content positively correlated with increase in hexose phosphate and total adenine nucleotides (FIGS. 16 E and F).

Figure 17:
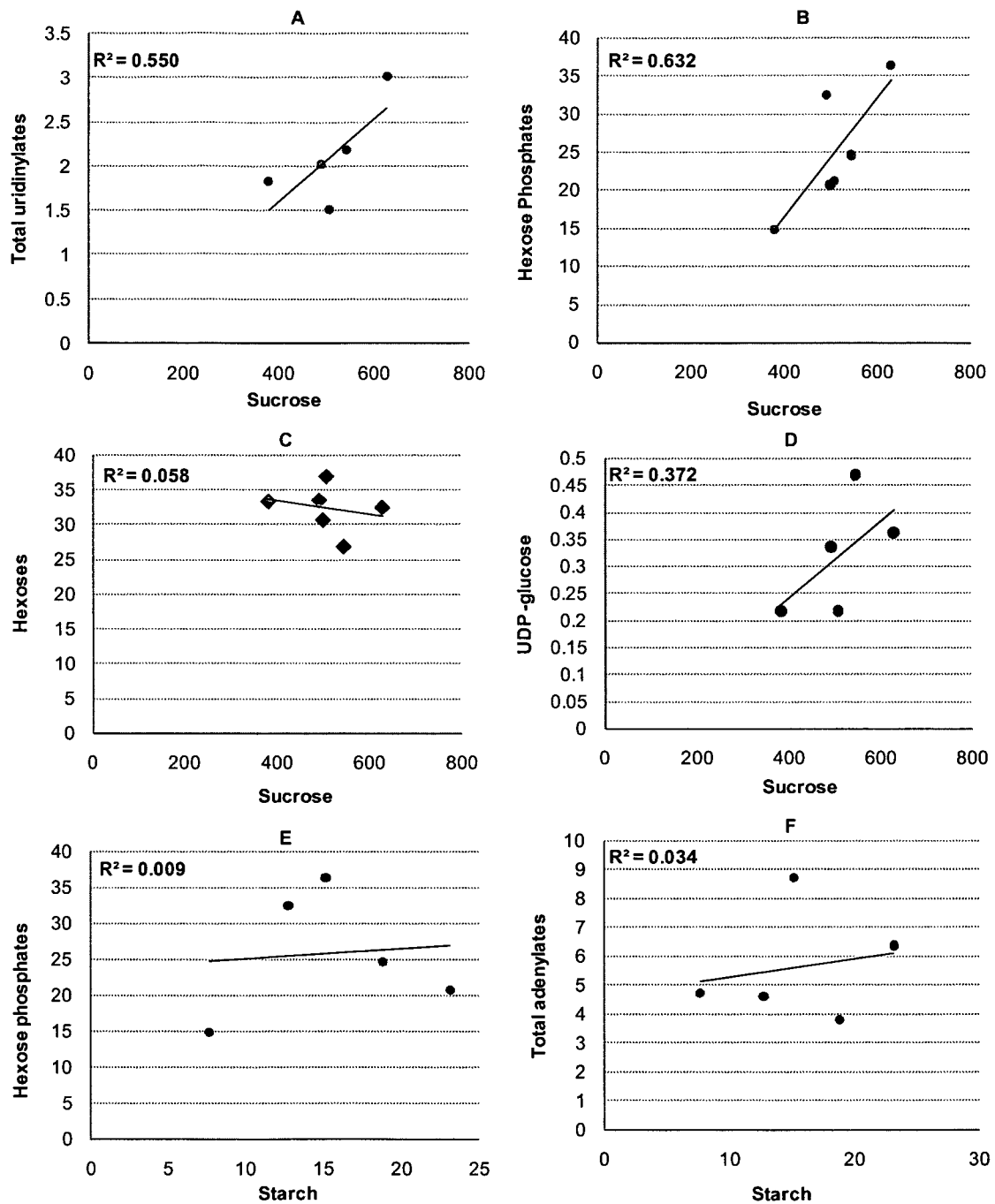
FIG. 17 shows linear correlations of metabolites involved in sucrose and starch metabolism in mature internodes. Apart from sucrose, starch and hexoses (μmol/g FW) all metabolite levels are given in nmol/g FW. For sucrose, (A) total uridinylates, (B) hexose phosphates, (C) hexoses, (D) UDP-glucose; for starch, (E) hexose phosphates, and (F) total adenylates. Data are mean of three independent plants per line.

In the internodes, a significant positives correlation was observed in all transgenic lines between sucrose and both total uridinylates and hexose phosphates (FIGS. 17 A and B, respectively). Sucrose and both hexose and UDP-glucose, as well as starch and both hexose phosphates and total adenyltes, on the other hand, demonstrated very weak correlations in all plants (FIG. 17).

3.3.6 Metabolites and Key Enzymes Analyses Using Linear Correlation

Figure 18:
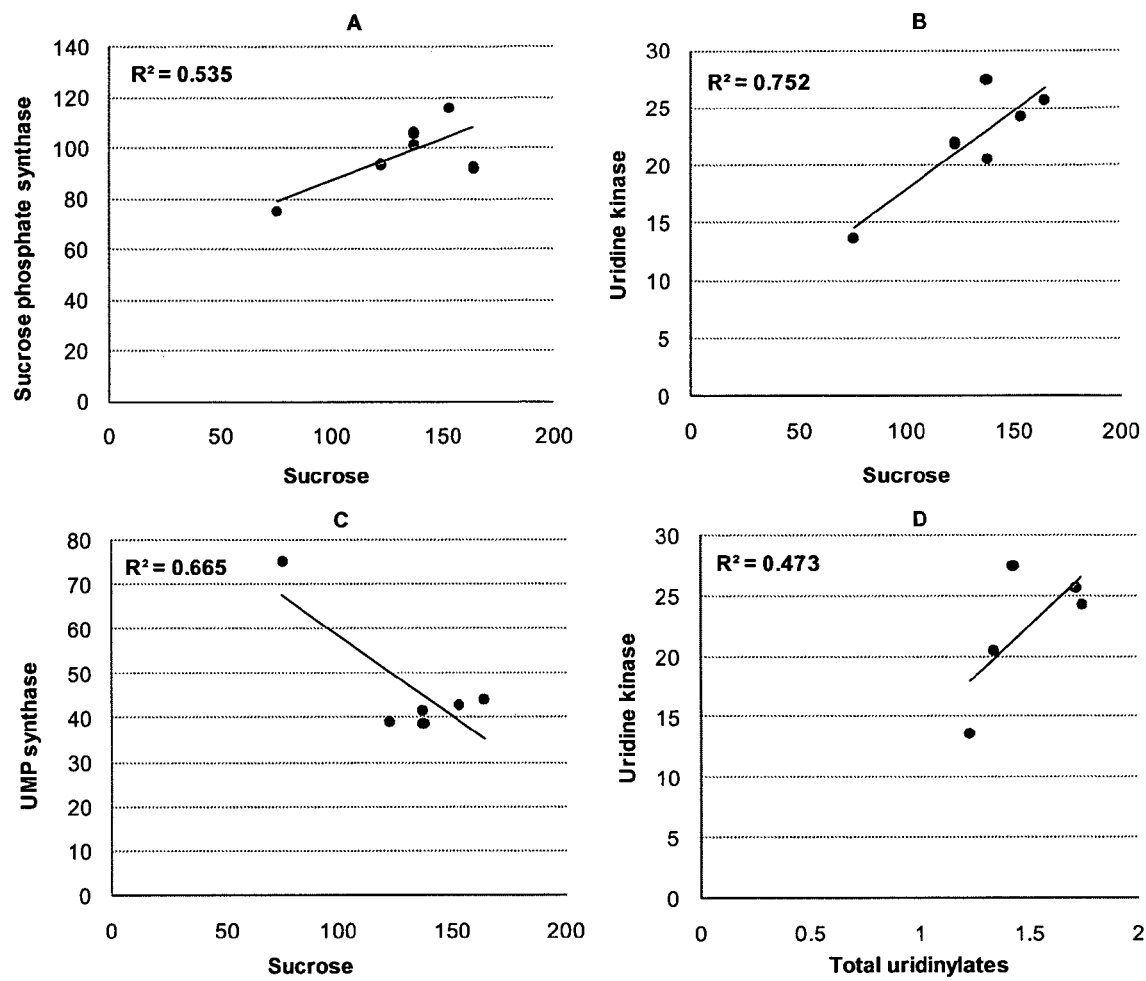
FIG. 18 shows linear correlations of metabolites and key enzymes in suspension cells. Apart from sucrose (μmol/g FW) all metabolites levels are given in nmol/g FW and all enzyme activities are expressed in $nmol.min^{-1}mg^{-1}$ protein; (A) sucrose and sucrose phosphate synthase, (B) uridine kinase, (C) sucrose and UMP synthase and (D) total uridinylates and uridine kinase. Data are mean of three replicates of the wild type and transgenic lines.

Sucrose and total uridinylates were plotted against the activities of key enzymes to determine a possible relationship in both the suspension cells and mature internodes. In the suspension cells, a significant positive correlation was observed between sucrose content and both sucrose phosphate synthase and uridine kinase activities (FIGS. 18 A and B, respectively). However, increase in sucrose content negatively correlated with changes in UMP synthase activity in all transgenic lines (FIG. 18 C; P=0.665).

Figure 19:
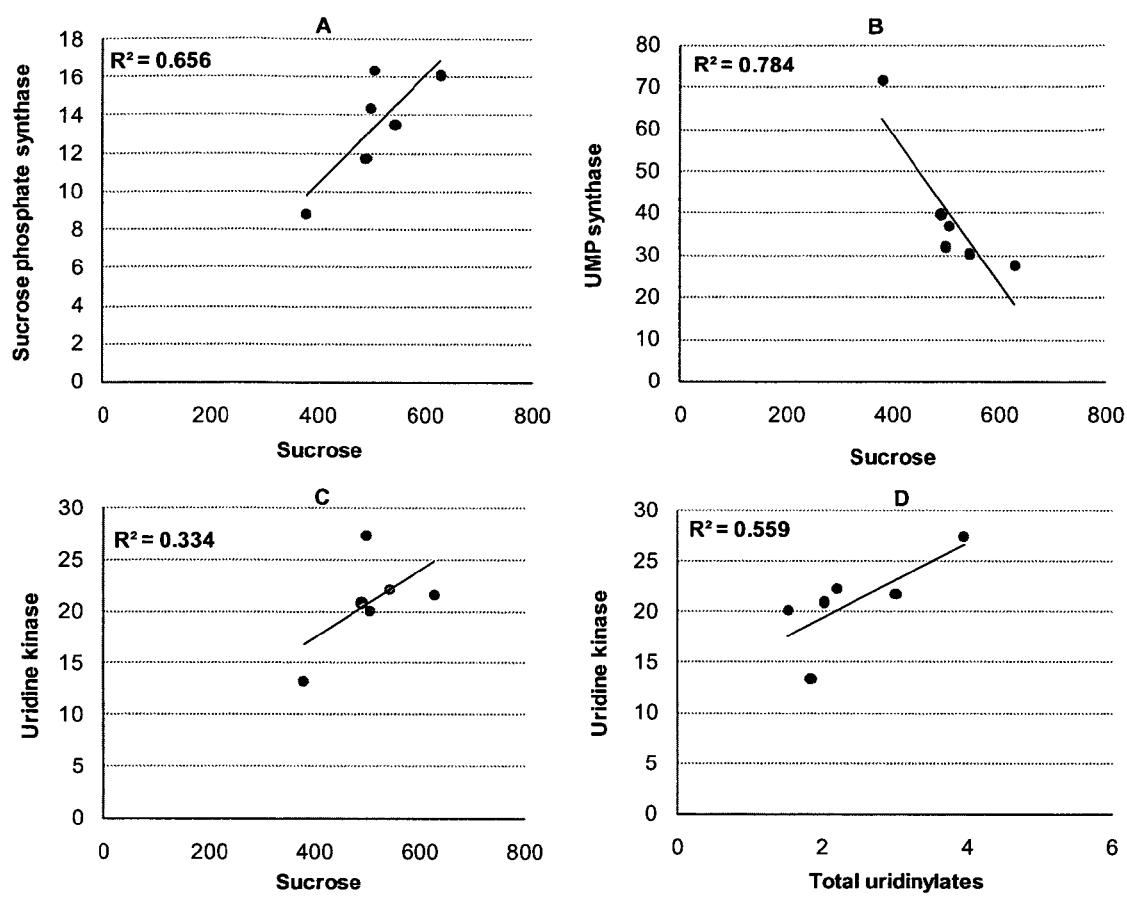
FIG. 19 shows linear correlations of metabolites and key enzymes in mature internodes. Apart from sucrose (μmol/g FW) all metabolites levels are given in nmol/g FW and all enzyme activities are expressed in $nmol.min^{-1}mg^{-1}$ protein; (A) sucrose and sucrose phosphate synthase, (B) sucrose and UMP synthase, (C) uridine kinase, and (D) total uridinylates and uridine kinase. Data are mean of three replicates of the wild type and transgenic lines.

In the internodes, a similar pattern was observed; an up-regulation of sucrose phosphate synthase activity positively correlated with changes in sucrose accumulation, and a decrease in UMP synthase activity negatively correlated with changes in sucrose content (FIGS. 19 A and B, P=0.656 and P=0.784, respectively). In contrast, an increase in uridine kinase activity did not show a significant correlation with changes in sucrose content; however, changes in uridine kinase positively correlated with an increase in total uridinylates (FIGS. 19 C and D, respectively).

3.3.5 Bioinformatic Analysis of Sugarcane UMPS

The BLAST search for DNA sequences showing high similarity to the DNA sequence of sugarcane UMPS (TC68130) revealed DNA encoding UMPS enzymes from other sugar-storing plants such as sweet sorghum (FIG. 16). The DNA sequence of sweet sorghum (XM_002456891.1) was aligned with that of sugarcane and showed high similarity (85.5%) (FIG. 17).

4. Discussion

In the work shown here, intron-spliced hairpin RNA vector technology was used to construct an RNAi vector for sugarcane embryonic calli transformation. Five lines transformed with the ihpRNA vector (pihUMPS) were generated. To assess the effect of repressed UMP synthase, the enzyme activities and metabolite levels of pathways surrounding the main carbohydrates, starch and sucrose, were determined. PCR and RT-PCR analyses confirmed the integration of the construct into the sugarcane transgenic lines, and indicated that the transformed lines had decreased the UMP synthase transcript level, respectively. Protein assays showed a repression of up to 62% of the activity of UMP synthase, which correlated well with transcript level found in all transgenic lines compare to the untransformed wild-type control.

The data demonstrated that repression of UMP synthase activity in transgenic sugarcane plants led to significant up-regulation of one of the pyrimidine salvage enzymes (UK), increases in sucrose, UDP-glucose, starch, and in the concentration of the hexose phosphate pools, as well as SPS, the main enzyme responsible for sucrose synthesis. The work described illustrates a method of obtaining a sugarcane crop with higher content in both sucrose and starch.

It will, however, be appreciated by those skilled in the art that the method described in the current invention may exhibit further characteristics besides the modification of the carbohydrate content of a plant; it will further be appreciated that modifications may be introduced to the method without diverging beyond the scope of the invention.

5. References

Ashihara, H., Stasolla, C., Loukanina, N., and Thorpe, T. A (2000). Purine and pyrimidine metabolism in cultured white spruce (*Picea glauca*) cells: Metabolic fate of 14C-labeled precursors and activity of key enzymes. *Physiol. Plant.* 108, 25-33

Baxter C J, Foyer C H, Turner J, Rolfe S A, Quick W P (2003). Elevated sucrose-phosphate synthase activity in transgenic tobacco sustains photosynthesis in older leaves and alters development. *Journal of Experimental Botany* 54, 1813-20.

Bergmeyer H U and Bernt E (1974) Sucrose. In *Methods of Enzymatic Analysis*, vol. 3 (Eds Bergmeyer HU) pp. 1176-1179. (Verlag Chemie Weinheim, Academic Press Inc., New York, London)

Bradford, M. M. (1976) A rapid and sensitive method for the quantification of microgram quantities of protein utilizing the principle of protein-dye binding. *Anal. Biochem.* 72, 248

Chakraborty S, Chakraborty N, Datta A (2000) Increase nutritive value of transgenic potato by expressing a nonallergic seed albumin gene from *Amaranthus hypochondriacus. Proc. natl. Acad. Sci. USA* 97, 3724-3729.

Geigenberger P, Regierer B, Nunes-Nesi A, Leisse A, Urbanczyk-Wochniak E, Springer F, van Dongen J T, Kossmann J (2005) Inhibition of de novo pyrimidine synthesis in growing potato tubers leads to a compensatory stimulation of pyrimidine salvage pathway and subsequent increase in biosynthetic performance. *Plant Cell* 17, 2077-2088.

Schäfer W. E, Rohwer J. M and Botha F. C (2004) Partial purification and characterisation of sucrose synthase in sugarcane. *Journal of Plant Physiology* 162, 11-20.

Sonnewald U, Hajirezaei, M. R. Kossmann, J. Heyer, A., Trethewey, R. N. and Willmitzer, L. (1997) Expression of a yeast invertase in potato tuber increases tuber size. *Natural Biotechnology* 15, 794-797.

Stark, D. M., Timmerman, K. P., Barry, G. F., Preiss, J., Kishore, G. M. (1992) Regulation of the amount of starch in plant tissues by ADP-glucose pyrophosphorylase. *Science* 258, 287-292.

Tabe I, Higgins T J V (1998) Engineering plant protein composition for improved nutrition. *Trend in Plant Science* 3, 282-286.

SEQUENCE LISTING

<160> NUMBER OF SEQ ID NOS: 2

<210> SEQ ID NO 1
<211> LENGTH: 880
<212> TYPE: DNA
<213> ORGANISM: Saccharum sp.

<400> SEQUENCE: 1

```
gtcaccacag aagcactggt gaaaagcatt acgtgaagac aagttaagca cacgcggagt        60
tttcggcatc gacagcatca caatgcctaa ctcaaccaac aagaacggag tgaaccaaga       120
```

```
ggaaattatt ctaacacaaa cgatgatgga gcatgctctg gatgagtctc ctctgcagtg      180
agtctgattg caattaggtc ctgactcgac tgtaggggga cctttccgca tgctcttatt      240
acgccaaacg cttggatttg cccacttgga atgcttacgg cgcccctca tagcaagctg       300 ttcttgtatg cctgccaccc ttgcaagcgg tactcccatg ccgtcttcat aggatcgcta      360
gcctttataa tcccgcgtcc aactatgatt atgtcgctgc ccctgtagtt tatcacagac      420
tcaggagtgt tgtattgttg cccaagatca tctcctccag cgaccatctg aactccaggt      480
gtggcatgga taaacgccgg gcttgatggt gttactgacc aagatgcagg atttactgag      540
ataaatccca tcacaaaatc agaatgttgc tcagcaatct ttacagcagc agcagtgtaa      600
tctccatgag caaggttgcc agcagagctc atctcagcga gcagaagtag ccctcttcct      660
tttggcaaac ccttcagctt caagccatct atgattccag gtccaggtac tatatgcgca      720
ttaacaatat cggcccagtc caatatgcgg aatactcctc cttcatattg catggtcact      780
gtatttccaa tgtcagcaaa cttgcggtct tcaaagatca agaagttgtg cttctcagca      840
atcgagcgga gcttagagcc aaaatcaggt gtaaaatcag                            880

<210> SEQ ID NO 2
<211> LENGTH: 880
<212> TYPE: DNA
<213> ORGANISM: Saccharum sp.

<400> SEQUENCE: 2
ctgattttac acctgatttt ggctctaagc tccgctcgat tgctgagaag cacaacttct       60
tgatctttga agaccgcaag tttgctgaca ttggaaatac agtgaccatg caatatgaag      120
gaggagtatt ccgcatattg gactgggccg atattgttaa tgcgcatata gtacctggac      180
ctggaatcat agatggcttg aagctgaagg gtttgccaaa aggaagaggg ctacttctgc      240
tcgctgagat gagctctgct ggcaaccttg ctcatggaga ttacactgct gctgctgtaa      300
agattgctga gcaacattct gattttgtga tgggatttat ctcagtaaat cctgcatctt      360
ggtcagtaac accatcaagc ccggcgttta tccatgccac acctggagtt cagatggtcg      420
ctggaggaga tgatcttggg caacaataca acactcctga gtctgtgata aactacaggg      480
gcagcgacat aatcatagtt ggacgcggga ttataaaggc tagcgatcct atgaagacgg      540
catgggagta ccgcttgcaa gggtggcagg catacaagaa cagcttgcta tgaggggcg       600 ccgtaagcat tccaagtggg caaatccaag cgtttggcgt aataagagca tgcggaaagg      660 tcccctaca gtcgagtcag gacctaattg caatcagact cactgcagag gagactcatc       720
cagagcatgc tccatcatcg tttgtgttag aataatttcc tcttggttca ctccgttctt      780
gttggttgag ttaggcattg tgatgctgtc gatgccgaaa actccgcgtg tgcttaactt      840
gtcttcacgt aatgcttttc accagtgctt ctgtggtgac                            880
```

The invention claimed is:

1. A method of increasing the sucrose content in one or more plant cells of a sugarcane plant, a sweet sorghum plant, or a sugar beet plant, the method comprising inserting into said one or more plant cells at least one exogenous nucleic acid, wherein the at least one exogenous nucleic acid comprises:
(i) at least 20 nucleotides of an antisense sequence of a uridine monophosphate synthase (UMPS) open reading frame (ORF):
(iii) at least 20 nucleotides of a sense sequence of a UMPS ORF: and/or
(iii) (i) as above, and (ii) as above, optionally with a spliceable intron sequence between (i) and (ii), and wherein the spliceable intron sequence is at least 70 by in length and the nucleotide sequence of (i) and the nucleotide sequence of (ii) are complementary to one another, thereby increasing the sucrose content in said sugarcane plant, said sweet sorghum plant, or said sugar beet plant.

2. The method according to claim 1, wherein the at least one exogenous nucleic acid is comprised in at least one gene silencing cassette.

3. The method according to claim 2, wherein the at least one gene silencing cassette is inserted into a population of cells of a sugarcane plant, a sweet sorghum plant, or a sugar beet plant.

4. The method according to claim 1, wherein a transgenic plant is regenerated from the one or more plant cells comprising said exogenous nucleic acid.

5. The method according to claim 1, wherein the method further comprises producing tissue having increased sucrose content from the one or more transformed cells of said sugarcane plant, said sweet sorghum plant, or said sugar beet plant.

6. A method of increasing the sucrose content in tissue of a sugarcane plant, a sweet sorghum plant, or a sugar beet plant, the method comprising producing one or more transformed cells of a sugarcane plant, a sweet sorghum plant, or a sugar beet plant according to the method of claim 1 and producing a tissue from said plant cells, wherein said tissue has increased sucrose content.

7. The method according to claim 6, wherein one or more transgenic plants are regenerated from the transformed cell of the sugarcane plant, the sweet sorghum plant, or the sugar beet plant.

8. The method according to claim 6 wherein the plant tissue is a callus.

9. The method according to claim 2, wherein the exogenous nucleic acid comprised in said at least one gene silencing cassette is operably linked to one or more transcription elements for transcribing the nucleic acid in the one or more plant cells.

10. The method according to claim 1, wherein the at least one exogenous nucleic acid comprises:
(i) a nucleotide sequence at least 95% similar to the nucleotide sequence of SEQ ID NO:1;
(ii) a nucleotide sequence at least 95% similar to the nucleotide sequence of SEQ ID NO:2; and/or
(iii) (i) as above, and (ii) as above, optionally with a spliceable intron sequence between (i) and (ii), and wherein the spliceable intron sequence is at least 70 by in length and the nucleotide sequence of (i) and the nucleotide sequence of (ii) are complementary to one another.

11. The method according to claim 9, wherein the UMPS ORF corresponds to the UMPS ORF of the transformed plant cell.

12. The method according to claim 1, wherein two or more gene silencing cassettes are inserted into said one or more plant cells of a sugarcane plant, a sweet sorghum plant, or a sugar beet plant.

13. The method according to claim 9, wherein the one or more transcription elements comprise a promoter.

14. The method according to claim 13 wherein the promoter is a monocotyledonous promoter.

15. The method of claim 2, wherein the one or more gene silencing cassettes are comprised in a vector.

16. The method according to claim 15, wherein the vector is an RNAi vector comprising an intron containing hairpin RNA ihpRNA.

17. The method according to claim 15, wherein the at least one exogenous nucleic acid is operably linked to one or more transcription elements for transcribing the nucleic acid.

18. A transformed sugarcane plant, sweet sorghum plant, sugar beet plant, plant part, or plant cell, wherein the plant, plant part or cell comprises
at least one exogenous nucleic acid comprising:
(i) at least 20 nucleotides of an antisense sequence of a uridine monophosphate synthase (UMPS) open reading frame (ORF);
(ii) at least 20 nucleotides of a sense sequence of a UMPS ORF; and/or
(iii) (i) as above, and (ii) as above, optionally with a spliceable intron sequence between (i) and (ii), and wherein the spliceable intron sequence is at least 70 by in length and the nucleotide sequence of (i) and the nucleotide sequence of (ii) are complementary to one another.

19. The transformed sugarcane plant, sweet sorghum plant, sugar beet plant, plant part, or plant cell according to claim 18, wherein the at least one exogenous nucleic acid is comprised in at least one gene silencing cassette.

20. The transformed sugarcane plant, sweet sorghum plant, sugar beet plant, plant part, or plant cell according to claim 18, wherein the exogenous nucleic acid is operably linked to one or more transcription elements for transcribing said nucleic acid and said exogenous nucleic acid is comprised in one or more gene silencing cassettes.

21. The transformed sugarcane plant, sweet sorghum plant, sugar beet plant, plant part, or plant cell according to claim 18, wherein the nucleic acid comprises:
(i) a nucleotide sequence at least 95% similar to the nucleotide sequence of SEQ ID NO:1;
(ii) a nucleotide sequence at least 95% similar to the nucleotide sequence of SEQ ID NO:2; and/or
(iii) (i) as above, and (ii) as above, optionally with a spliceable intron sequence between (i) and (ii), and wherein the spliceable intron sequence is at least 70 by in length and the nucleotide sequence of (i) and the nucleotide sequence of (ii) are complementary to one another.

22. The transformed sugarcane plant, sweet sorghum plant, sugar beet plant, plant part, or plant cell according to claim 20, wherein the one or more transcription elements comprise a promoter.

23. The transformed sugarcane plant, sweet sorghum plant, sugar beet plant, plant part, or plant cell according to claim 22, wherein the promoter is a monocotyledonous promoter.

24. A plant comprising or derived from the transformed plant, plant part or plant cell of the sugarcane plant, a sweet sorghum plant, or a sugar beet plant of claim 18.

25. The transformed sugarcane plant, sweet sorghum plant, sugar beet plant, plant part, or plant cell according to claim 19, wherein the at least one expression cassette is comprised in a vector.

26. The transformed sugarcane plant, sweet sorghum plant, sugar beet plant, plant part, or plant cell according to claim 18, wherein the transformed plant part is a callus.

27. The transformed sugarcane plant, sweet sorghum plant, sugar beet plant, plant part, or plant cell according to claim 25, wherein the vector is an RNAi vector comprising ihpRNA.

* * * * *

UNITED STATES PATENT AND TRADEMARK OFFICE
CERTIFICATE OF CORRECTION

PATENT NO. : 8,729,338 B2  
APPLICATION NO. : 13/496468  
DATED : May 20, 2014  
INVENTOR(S) : Boussiengui-Boussiengui et al.

Page 1 of 1

It is certified that error appears in the above-identified patent and that said Letters Patent is hereby corrected as shown below:

On Title Page:
Item 73, Assignees: Please correct "South African Sugarcane Research Institute, Mouth Edgecombe (ZA)"
to read
-- South African Sugarcane Research Institute, Mount Edgecombe (ZA) --

In the Claims:
Column 22, Claim 1, Line 59: Please correct "at least 70 by in length"
        to read -- at least 70 bp in length --

Column 23, Claim 10, Line 39: Please correct "at least 70 by in length"
        to read -- at least 70 bp in length --

Column 23, Claim 16, Line 57: Please correct "ihpRNA."
        to read -- (ihpRNA). --

Column 24, Claim 18, Line 12: Please correct "at least 70 by in length"
        to read -- at least 70 bp in length --

Column 24, Claim 21, Line 36: Please correct "at least 70 by in length"
        to read -- at least 70 bp in length --

Signed and Sealed this
Twenty-third Day of December, 2014

Michelle K. Lee
*Deputy Director of the United States Patent and Trademark Office*